(12) United States Patent
Bachar

(10) Patent No.: US 10,271,853 B2
(45) Date of Patent: Apr. 30, 2019

(54) LAPAROSCOPIC CLIP APPLIER

(71) Applicant: CLIPTIP MEDICAL LTD., Yokneam Illit (IL)

(72) Inventor: Yehuda Bachar, Givat Shmuel (IL)

(73) Assignee: CLIPTIP MEDICAL LTD., Yokneam Illit (IL)

(*) Notice: Subject to any disclaimer, the term of this patent is extended or adjusted under 35 U.S.C. 154(b) by 369 days.

(21) Appl. No.: 15/022,832

(22) PCT Filed: Sep. 18, 2014

(86) PCT No.: PCT/IL2014/050838
§ 371 (c)(1),
(2) Date: Mar. 17, 2016

(87) PCT Pub. No.: WO2015/040621
PCT Pub. Date: Mar. 26, 2015

(65) Prior Publication Data
US 2016/0317157 A1 Nov. 3, 2016

Related U.S. Application Data

(60) Provisional application No. 61/879,256, filed on Sep. 18, 2013.

(51) Int. Cl.
*A61B 17/10* (2006.01)
*A61B 17/128* (2006.01)
(Continued)

(52) U.S. Cl.
CPC .... *A61B 17/1285* (2013.01); *A61B 17/00234* (2013.01); *A61B 17/128* (2013.01); *A61B 17/1227* (2013.01); *A61B 2017/00867* (2013.01)

(58) Field of Classification Search
CPC .......... A61B 17/00234; A61B 17/0409; A61B 17/064; A61B 17/0642; A61B 17/068; A61B 17/07207; A61B 17/12; A61B 17/122; A61B 17/1222; A61B 17/1227; A61B 17/128; A61B 17/1285; A61B 17/3417; A61B 17/3468; A61B 17/349; A61B 17/10; A61B 2017/00867;
(Continued)

(56) References Cited

U.S. PATENT DOCUMENTS 4,934,364 A 6/1990 Green
5,222,961 A 6/1993 Nakao et al.
(Continued)

FOREIGN PATENT DOCUMENTS

JP S63267345 A 11/1988
WO 2008073567 A1 6/2008

OTHER PUBLICATIONS

International Search Report of PCT/IL2014/050838 Completed Mar. 4, 2015; dated Mar. 8, 2015 10 Pages.
(Continued)

*Primary Examiner* — Elizabeth Houston
*Assistant Examiner* — Kankindi Rwego

(57) ABSTRACT

A laparoscopic clip applier comprising multiple clips housed in a rigid sleeve, where the arms of the clips are oriented lengthwise in the sleeve, and a deployment mechanism for deploying the clips from a distal end of the sleeve via a perforation made by a needle provided with the distal end of the sleeve.

18 Claims, 18 Drawing Sheets

(51) Int. Cl.
*A61B 17/00* (2006.01)
*A61B 17/122* (2006.01)

(58) Field of Classification Search
CPC .... A61B 2017/0646; A61B 2017/0647; A61B 2017/0648; A61B 2017/0649; A61B 2017/12004
See application file for complete search history.

(56) References Cited

U.S. PATENT DOCUMENTS

| | | | |
|---|---|---|---|
| 5,484,451 A * | 1/1996 | Akopov | A61B 17/04 227/175.1 |
| 7,942,885 B2 | 5/2011 | Sixto, Jr. et al. | |
| 8,062,311 B2 | 11/2011 | Litscher et al. | |
| 2002/0133178 A1 | 9/2002 | Muramatsu et al. | |
| 2004/0193189 A1 | 9/2004 | Kortenbach et al. | |
| 2005/0107809 A1 | 5/2005 | Litscher et al. | |
| 2010/0191260 A1 * | 7/2010 | Mohajer | A61B 17/3474 606/144 |

OTHER PUBLICATIONS

Written Opinion of of PCT/IL2014/050838 Completed Mar. 4, 2015; dated Mar. 8, 2015 8 Pages.

* cited by examiner

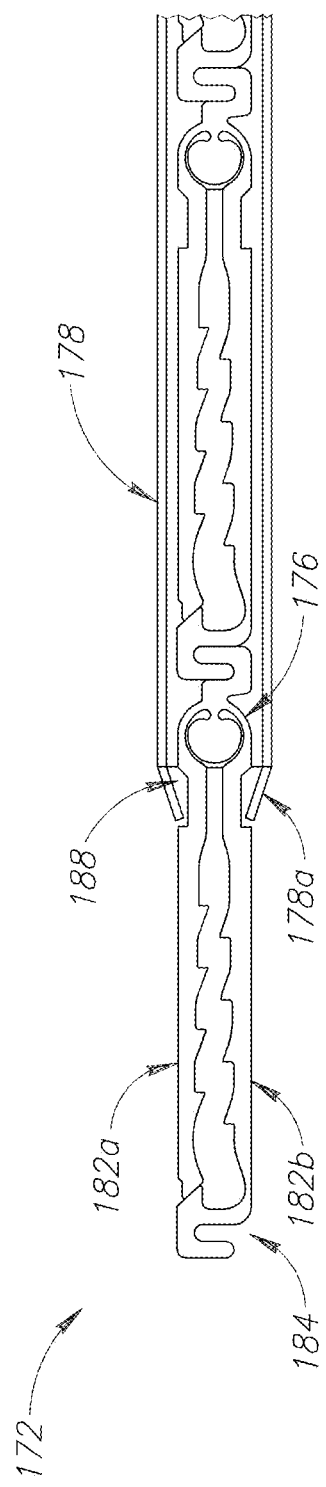

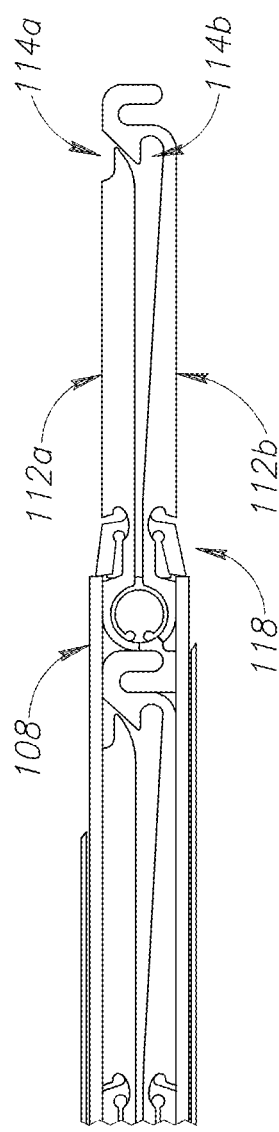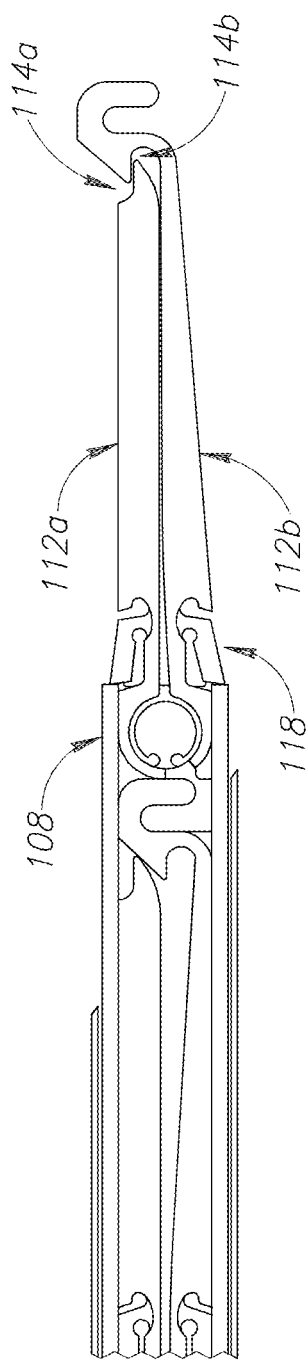

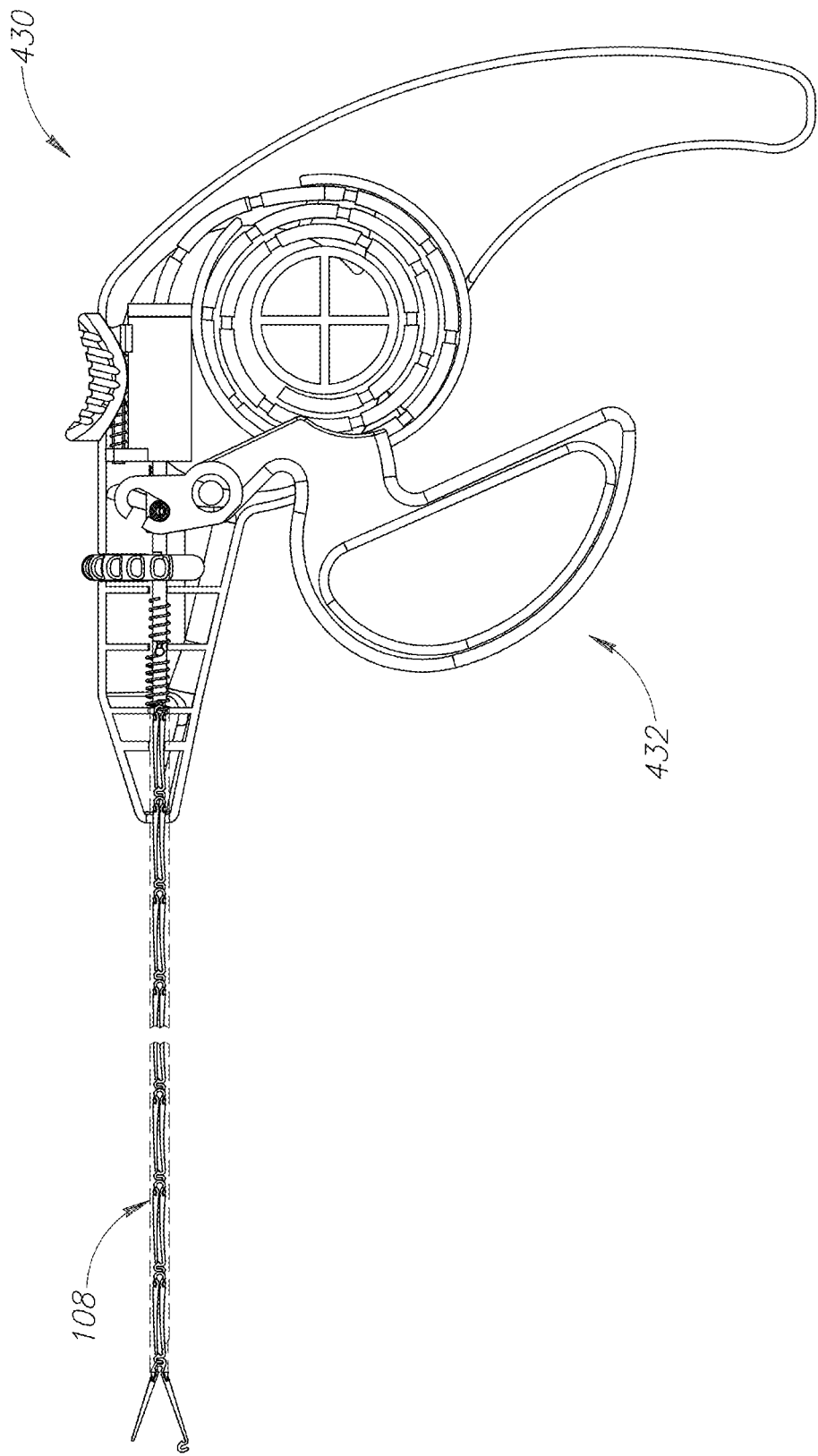

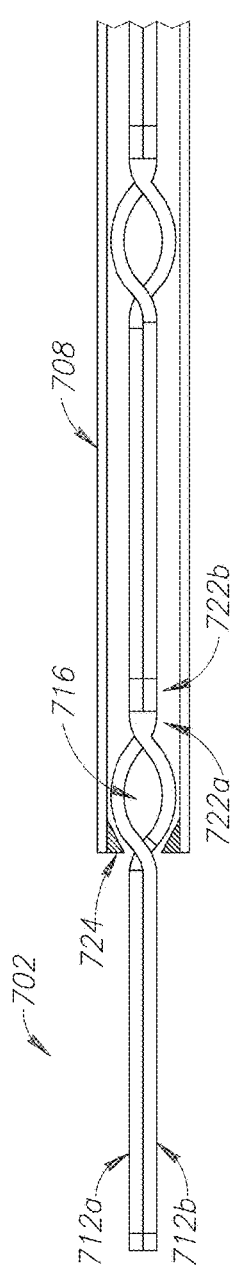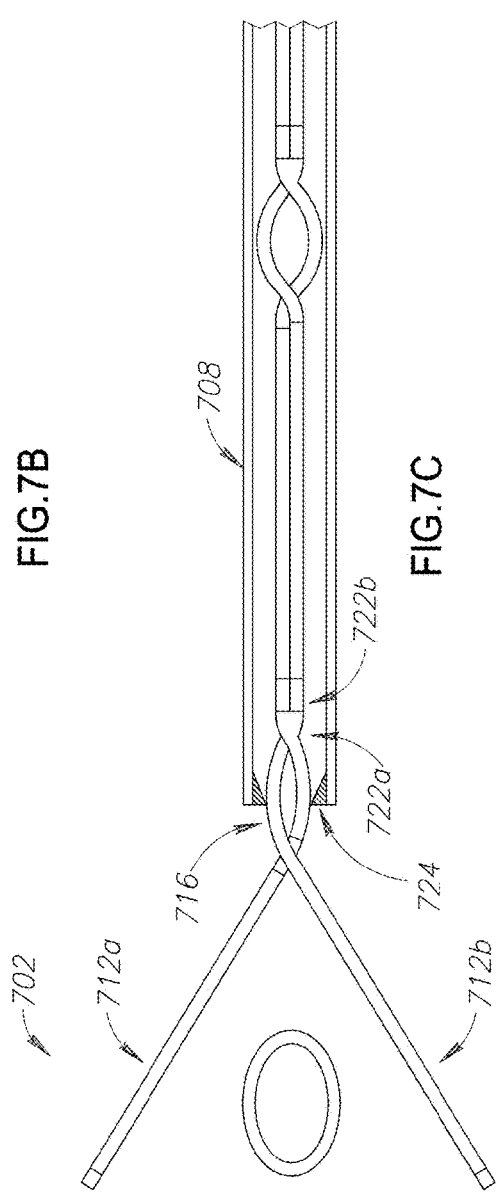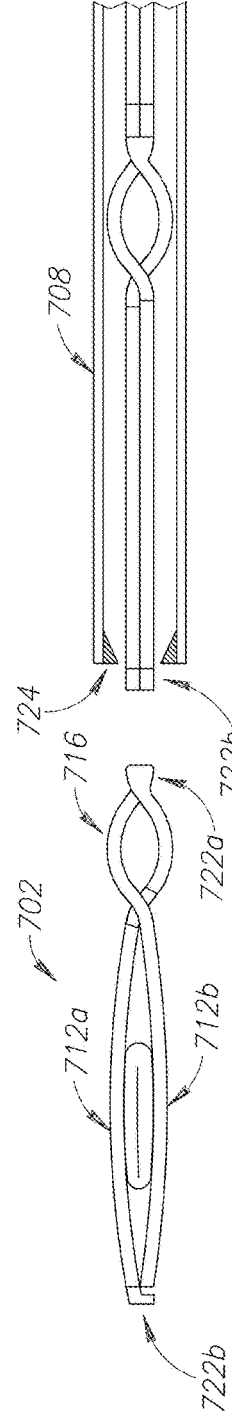

LAPAROSCOPIC CLIP APPLIER

CROSS REFERENCE TO RELATED APPLICATIONS

This application claims the benefit of U.S. Provisional Patent Application No. 61/879,256, filed Sep. 18, 2013 and entitled "Laparoscopic Clip Applier", which is incorporated herein by reference in its entirety.

FIELD OF THE INVENTION

The invention relates to the field of surgical clip application.

BACKGROUND

In order to operate on a given tissue or a blood vessel, surgeons must ligate or occlude nearby blood vessels to prevent patient blood loss. Surgeons employ small surgical clips and long cartridges within the clip appliers to ligate or occlude blood vessels, or other tubular structures such as but not limited to cystic duct, uterine tubes, etc, in laparoscopic and endoscopic surgical procedures. These surgical clips need to perform multiple functions.

First, the surgical clip must be securely located on the blood vessel. Movement or slippage of the surgical clip on the vessel should be minimized or eliminated once the clip has been applied. Second, the surgical clip should completely close the blood vessel to which it is applied. Movement or slippage of the surgical clip or failure to fully close a blood vessel may cause blood loss, a lethal drop in blood pressure, or result in a hematoma that may cause pressure on surrounding tissue, or local infection. Third, the surgical clip should be designed to minimize damage to the closed blood vessel and surrounding tissue as much as possible. Surgical clips that cause tissue or blood vessel damage may result in internal bleeding, a lethal drop in blood pressure, infections, or longer recovery periods.

There are a variety of medical devices and procedures used for applying surgical clips. Typically they require one or more surgical incisions, prolonging recovery and leading to potential complications, such as infections.

Laparoscopic surgery is an increasingly popular form of surgery. In laparoscopic surgery, several small incisions are made in the patient's abdomen and a tube, or a trocar, is inserted through each incision. These trocars often range in size between 5, 8, 10 and 12 mm in diameter. The surgical instruments, including staple or clip applicators and extractors, are inserted through the trocars. Laparoscopic procedures generally require that any instrumentation inserted into the body be sealed, i.e., provisions must be made to ensure that gases do not enter or exit the body through the laparoscopic incision as, for example, in surgical procedures in which the surgical region is insufflated. The incisions that are performed in order to introduce the trocars, may cause postoperative pain; prolonged recovery, and scars. Additionally, these incisions may results in local hernia, or weakness of abdominal wall and local infections.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a laparoscopic clip applier comprising: a handle, a rigid sleeve extending from the handle, multiple interconnected clips, each being normally-open by a proximal spring integral to the clip, where the clips are housed in the sleeve, and where the clips are provided with a self-locking mechanism at their distal end, and where each of the clips, when housed within the sleeve, is closed and unlocked, and a deployment mechanism operable by the handle and configured to: advance the clips towards a distal end of the sleeve, thereby positioning a most distally-positioned clip of the clips for deployment by exposing the clip from the distal end of the sleeve, where the exposing causes the most distally-positioned clip to open, advance the sleeve relative to the exposed clip to close the exposed clip over a bodily tissue until the self-locking mechanism of the exposed clip engages, thereby deploying the exposed clip, and retract the sleeve relative to the exposed clip, thereby exposing an interconnecting mechanism disposed at a proximal end of the exposed clip, to enable disconnecting the exposed clip from the clips housed in the sleeve.

In some embodiments, the clip applier further comprises a Veress needle comprising: the rigid sleeve, and an outer sleeve with a sharp distal end, where the distal end of the most distally-positioned clip provides a blunt distal end for the rigid sleeve, and where the clips are deployed via a perforation made by the sharp distal end.

In some embodiments, the clip applier further comprises one or more prongs, where the self-locking mechanism is activated by a moment applied on the exposed clip by the prongs.

In some embodiments, the prongs are disposed with the inner sleeve, and where the self-locking mechanism is activated by engaging the prongs with one or more niches provided with the exposed clip.

In some embodiments, the prongs are disposed with a pair of arms of the clip, and where the self-locking mechanism is activated by engaging the prongs with the advancing sleeve.

In some embodiments, the self-locking mechanism comprises an elastic hook disposed at a distal end of a clip arm of the exposed clip, where the elastic hook is biased outwards, and where the elastic hook is folded inwards when the clip is housed within the sleeve and protrudes outwards when the clip is exposed from the sleeve.

In some embodiments, a length of the elastic hook is greater than an inner diameter of the sleeve.

In some embodiments, the deployment mechanism includes a pusher for advancing the clips, where a proximal portion of the pusher is alternately flexible for bending into a coil configuration and allowing the pusher to be housed in the handle, and a distal portion of the pusher is alternately straight and rigid for advancing the clips in the sleeve.

In some embodiments, the deployment mechanism includes one or more protrusions for engaging the pusher to control movement of the pusher from the coil configuration to the straight rigid pusher for advancing the clips.

In some embodiments, the clip applier further comprises a dial for rotating the sleeve in synchrony with the clips, where a ball and socket joint provided with the pusher enables the handle to remain stationary relative to the rotated clips.

In some embodiments, a pair of clip arms of the interconnected clips housed in the sleeve are oriented lengthwise along a length of the sleeve.

In some embodiments, the clips are made, at least partially, of superelastic material.

In some embodiments, an axial distance between the exposed clip and the handle throughout the sleeve advancement steps remains constant.

In some embodiments, a diameter of the rigid sleeve is micro-laparoscopic.

In some embodiments, the clips are made of Nitinol.

There is further provided, in accordance with an embodiment, a laparoscopic clip applier comprising: a handle, a rigid sleeve extending from the handle, multiple interconnected, normally-closed clips where the clips are housed in the sleeve, and where each of the clips, when housed within the sleeve, is closed, and a deployment mechanism operable by the handle and configured to: advance the clips towards a distal end of the sleeve, thereby positioning a most distally-positioned clip of the clips for deployment by exposing the clip from the distal end of the sleeve, retract the sleeve relative to the exposed clip in a first step to open the exposed clip by compressing a hinge of the clip, retract the sleeve relative to the exposed clip in a second step to close the exposed clip over a bodily tissue, and retract the sleeve relative to the exposed clip to expose an interconnecting mechanism disposed at a proximal end of the exposed clip and enable disconnecting the exposed clip from the clips housed in the sleeve.

In some embodiments, the clip applier further comprises a Veress needle comprising: the rigid sleeve, and an outer sleeve with a sharp distal end, where the distal end of the most distally-positioned clip provides a blunt distal end for the rigid sleeve, and where the clips are deployed via a perforation made by the sharp distal end.

In some embodiments, the hinge is compressed by at least one protrusion disposed at the distal end of the retracting sleeve.

In some embodiments, the deployment mechanism includes a pusher for advancing the clips, where a portion of the pusher is alternately flexible for bending into a coil configuration allowing the pusher to be housed in the handle, and a distal portion of the pusher is alternately straight and rigid for advancing the clips in the sleeve.

In some embodiments, the deployment mechanism includes one or more protrusions for engaging the pusher to control the advancement of the pusher from the coil configuration to the straight rigid pusher for advancing the clips.

In some embodiments, the clip applier further comprises a dial for rotating the sleeve in synchrony with the clips, where a ball and socket joint provided with the pusher enables the handle to remain stationary relative to the rotated clips.

In some embodiments, a pair of clip arms of the interconnected clips are oriented lengthwise with the sleeve.

In some embodiments, the clips are made of superelastic material.

In some embodiments, an axial distance between the exposed clip and the handle throughout the sleeve retraction steps remains constant.

In some embodiments, a diameter of the rigid sleeve is micro-laparoscopic.

There is further provided, in accordance with an embodiment, a laparoscopic clip applier comprising: a handle, a rigid sleeve extending from the handle, multiple clips, that are normally-opened by a proximal spring, where the clips are housed in the sleeve, and where the clips are provided with a self locking mechanism at their distal end, and where each of the clips, when housed within the sleeve, is closed and unlocked, and a deployment mechanism operable by the handle and configured to: advance the clips towards a distal end of the sleeve, thereby positioning a most distally-positioned clip of the clips for deployment by exposing the clip from the distal end of the sleeve, where the exposing causes the most distally-positioned clip to open, advance the sleeve relative to the exposed clip to close the exposed clip over a bodily tissue until the self locking mechanism of the exposed clip engages, thereby deploying the exposed clip.

In some embodiments, a distance between the exposed clip and the handle throughout the moving, closing and locking steps remains constant.

In some embodiments, the clip applier further comprises a Veress needle comprising: the rigid sleeve, and an outer sleeve with a sharp distal end, where the distal end of the most distally-positioned clip provides a blunt distal end for the rigid sleeve, and where the clips are deployed via a perforation made by the sharp distal end.

In some embodiments, the deployment mechanism includes one or more ratchets for advancing and deploying the clips.

In some embodiments, the clip applier further comprises one or more prongs, where the self locking mechanism is activated by the prongs.

In some embodiments, the clips housed in the sleeve rotate in synchrony with a rotation of the sleeve.

In some embodiments, a pair of clip arms of the clips are oriented lengthwise with the sleeve.

In some embodiments, the clips are made of superelastic material.

In some embodiments, a diameter of the rigid sleeve is micro-laparoscopic.

There is further provided, in accordance with an embodiment, a laparoscopic clip applier comprising: multiple clips, a rigid sleeve housing the multiple clips, where a pair of clip arms of the clips are oriented lengthwise along a length of the sleeve, and a deployment mechanism for deploying the multiple clips from a distal end of the sleeve via a perforation made by a needle that is provided with the distal end of the sleeve.

In some embodiments, the sleeve and the needle form a Veress needle.

In some embodiments, the clip applier further comprises a handle for operating the deployment mechanism.

In some embodiments, the deployment mechanism includes a clip advancement mechanism for advancing the clips in the sleeve to expose a most distally positioned clip of the clips housed in the sleeve from the distal end of the sleeve.

In some embodiments, the deployment mechanism further comprises a sleeve maneuvering mechanism for advancing and retracting the sleeve with respect to the exposed clip, thereby controlling a deployment of the exposed clip.

In some embodiments, the clips are interconnected in the sleeve via a head disposed at a distal end of a proximal clip interconnected to a tail disposed at the proximal end of a distal clip.

In some embodiments, the clip advancement mechanism includes a pusher for advancing the clips in the sleeve where a proximal portion of the pusher is alternately flexible for bending into a coil configuration and allowing the pusher to be housed in the handle, and a distal portion is alternately straight and rigid for penetrating the sleeve to advance the clips in the sleeve.

In some embodiments, the clip applier further comprises a dial for rotating the sleeve in synchrony with the clips, where a ball and socket joint provided with the pusher enables the handle to remain stationary relative to the rotated clips.

In some embodiments, the clips are each normally-open and where the clips are housed in a closed and unlocked configuration in the sleeve.

In some embodiments, each of the clips includes a self-locking mechanism.

In some embodiments, the clip applier of further comprises one or more prongs for applying a moment to close the clips and activate the self-locking mechanism.

In some embodiments, the prong is disposed with the distal end of the sleeve and where the deployment mechanism deploys the clips by: advancing, via the clip advancement mechanism, the clips to expose a most distally positioned clip housed in the sleeve from the distal end of the sleeve, advancing, via the sleeve maneuvering system, the sleeve with respect to the exposed clip thereby engaging the prongs with a niche provided on a clip arm of the exposed clip and applying a moment that closes the clip arms until the self locking mechanism of the clip engages, thereby locking the clip over a bodily tissue, and retracting, via the sleeve maneuvering system, the sleeve with respect to the exposed clip, thereby exposing an interconnecting mechanism disposed at a proximal end of the exposed clip, to enable disconnecting the exposed clip from the clips housed in the sleeve.

In some embodiments, an axial distance between the exposed clip and the handle throughout the advancing and retracting the sleeve steps remains constant.

In some embodiments, the prong is disposed with a pair of clip arms provided with the clip, and where the deployment mechanism deploys the clips by advancing, via the clip advancement mechanism, the clips to expose the most distally positioned clip house in the sleeve from the distal end of the sleeve, advancing, via the sleeve maneuvering system, the sleeve with respect to the exposed clip thereby pushing the distal end of the sleeve against the prongs and applying a moment that closes the clip arms until the self locking mechanism of the clip engages, thereby locking the clip over a bodily tissue, and retracting, via the sleeve maneuvering system, the sleeve with respect to the exposed clip, thereby exposing an interconnecting mechanism disposed at a proximal end of the exposed clip, to enable disconnecting the exposed clip from the clips housed in the sleeve.

In some embodiments, an axial distance between the exposed clip and the handle throughout the advancing and retracting the sleeve steps remains constant.

In some embodiments, the self-locking mechanism comprises an elastic hook disposed at a distal end of a clip arm of the exposed clip, where the elastic hook is biased outwards, and where the elastic hook is folded inwards when the clip is housed within the sleeve and protrudes outwards when the clip is exposed from the sleeve, and where a length of the elastic hook is greater than a diameter of the sleeve.

In some embodiments, the clip advancement mechanism further comprises: a secondary sleeve, and multiple ratchets provided with the sleeves for advancing and deploying the clips housed in the sleeve.

In some embodiments, the clips are normally-closed and are housed in a closed configuration in the sleeve.

In some embodiments, the clip applier further comprises one or more protrusions at the distal end of the sleeve, and where the deployment mechanism deploys clips by: advancing, via the clip advancement mechanism, the clips housed in the sleeve to expose at least a portion of the most distally positioned clip in the sleeve from the distal end of the sleeve, retracting, via the sleeve maneuvering system, the sleeve with respect to the at least partially exposed clip to engage the protrusion with a clip hinge provided at a proximal end of the exposed clip, compressing the clip hinge, thereby opening the clip, retracting, via the sleeve maneuvering system, the sleeve with respect to the exposed clip to disengage the prong from the clip hinge, thereby closing the clip arms over a bodily tissue, and retracting, via the sleeve maneuvering system, the sleeve with respect to the exposed clip, thereby exposing an interconnecting mechanism disposed at a proximal end of the exposed clip, to enable disconnecting the exposed clip from the clips housed in the sleeve.

In some embodiments, an axial distance between the exposed clip and the handle throughout the advancing and retracting the sleeve steps remains constant.

In some embodiments, a diameter of the rigid sleeve is micro-laparoscopic.

There is further provided, in accordance with an embodiment, a surgical clip comprising: a pair of clip arms, a self-locking mechanism provided at a distal end of the arms, a hinge spring connecting the arms, where the hinge biases the arms open, an interconnecting head disposed at a distal end of the self-locking mechanism, and an interconnecting tail disposed at a proximal end of the hinge spring, where the interconnecting head and interconnecting tail enable interconnecting multiple ones of the clip.

In some embodiments, the clip arms provide with one or more prongs for engaging with the sleeve to activate the self-locking mechanism.

In some embodiments, the clip arms provide one or more niches for engaging with the sleeve to activate the self-locking mechanism.

In some embodiments, the self-locking mechanism comprises an elastic hook disposed at a distal end of a clip arm of the exposed clip, where the elastic hook is biased outwards, and where the elastic hook is folded inwards when the clip is housed within the sleeve and protrudes outwards when the clip is exposed from the sleeve.

There is further provided, in accordance with an embodiment, a surgical clip comprising: a pair of clip arms, a hinge spring connecting the arms, where the hinge biases the arms closed, and where the hinge spring is configured, when compressed, to open the clip arms, an interconnecting head disposed at the distal end of the clip arms, and an interconnecting tail disposed at the proximal end of the hinge spring, where the interconnecting head and the interconnecting tail enable interconnecting multiple ones of the clip.

There is further provided, in accordance with an embodiment, a method for deploying a clip using a laparoscopic clip applier, the method comprising: positioning a clip applier to deploy a surgical clip housed in a rigid sleeve provided with the clip applier, where the sleeve houses multiple interconnected surgical clips, where each of the clips, when housed within the sleeve, is closed and unlocked, and where the clip arms of the clip are aligned lengthwise with a length of the sleeve, and where the clip is provided with a self locking mechanism at its distal end and is normally-open by a proximal spring integral to the clip, operating a handle extending from the sleeve to: advance the clips towards a distal end of the sleeve, thereby position a most distally positioned clip for deployment by exposing the clip from the distal end of the sleeve, where the exposing causes the most distally-positioned clip to open, advance the sleeve relative to the exposed clip to close the exposed clip over a bodily tissue until the self locking mechanism of the exposed clip engages, thereby deploying the exposed clip, and retract the sleeve relative to the exposed clip to expose an interconnecting mechanism disposed at a proximal end of the exposed clip, to enable disconnecting the exposed clip from the clips housed in the sleeve.

In some embodiments, exposing the portion of the most distally positioned clip from the distal end of the sleeve further comprises perforating a body cavity wall with a Veress needle comprised in the clip applier, where the Veress needle comprises: the rigid sleeve, and an outer sleeve with a sharp distal end, where the distal end of the most distally-positioned clip provides a blunt distal end for the rigid sleeve, and where the clips are deployed via a perforation made by the sharp distal end.

In some embodiments, advancing the sleeve relative to the exposed clip to close and lock the exposed clip further comprises applying a moment on the clip via one or more prongs provided with the clip applier.

In some embodiments, the prongs are disposed with the inner sleeve, and where the self locking mechanism is activated by engaging the prongs with one or more niches provided with the clips.

In some embodiments, the prongs are disposed with a pair of arms of the exposed clip, and where the self locking mechanism is activated by engaging the prongs with the sleeve.

In some embodiments, engaging the self locking mechanism comprises engaging an elastic hook disposed at a distal end of a clip arm of the exposed clip with another clip arm of the exposed clips, where the elastic hook is biased outwards, and where the elastic hook is folded inwards when the clip is housed within the sleeve and protrudes outwards when the clip is exposed from the sleeve, and where a length of the elastic hook is greater than a diameter of the sleeve.

In some embodiments, advancing the clips further comprises advancing a pusher for advancing the clips, where a portion of the pusher is alternately flexible for bending into a coil configuration allowing it to be stored in the handle, and alternately straight and rigid for advancing the clips in the sleeve.

In some embodiments, the method further comprises one or more ratchets for engaging the pusher to control the advancement of the pusher from the coil configuration to the straight rigid pusher for advancing the clips.

In some embodiments, the method further comprises rotating a dial provided with the handle to rotate the clips housed in the sleeve in synchrony with a rotation of the sleeve, where a ball and socket joint provided with the pusher enables the handle to remain stationary relative to the rotated clips.

In some embodiments, the sleeve houses the interconnected clips with a pair of clip arms of the interconnected clips oriented lengthwise along a length of the sleeve.

In some embodiments, the sleeve houses the clips that are made of superelastic mater.

In some embodiments, an axial distance between the exposed clip and the handle throughout the sleeve advancement steps remains constant.

In some embodiments, a diameter of the rigid sleeve is micro-laparoscopic.

There is further provided, in accordance with an embodiment, a method for deploying a clip using a laparoscopic clip applier, the method comprising: positioning a clip applier to deploy a surgical clip housed in a rigid sleeve provided with the clip applier, where the sleeve houses multiple interconnected surgical clips that are each normally closed by a proximal spring integral to the clip, and where the clip, when housed within the sleeve, is closed, and operating a handle extending from the sleeve to advance the clips towards a distal end of the sleeve, thereby position a most distally positioned clip for deployment by exposing the clip from the distal end of the sleeve, retract the sleeve relative to the exposed clip in a first step to open the exposed clip by compressing the hinge of the clip, retract the sleeve relative to the exposed clip in a second step to close the exposed clip over a bodily tissue, and retract the sleeve relative to the exposed clip to exposing an interconnecting mechanism disposed at a proximal end of the exposed clip and enable disconnecting the exposed clip from the clips housed in the sleeve.

In some embodiments, exposing the portion of the most distally positioned clip from the distal end of the sleeve further comprises perforating a body cavity wall with a Veress needle provided with the clip applier, where the Veress needle includes the rigid sleeve, and an outer sleeve with a sharp distal end, where the distal end of the most distally-positioned clip provides a blunt distal end for the rigid sleeve, and where the clips are deployed via a perforation made by the sharp distal end.

In some embodiments, compressing the hinge comprises compressing by a protrusion disposed at the distal end of the retracting sleeve.

In some embodiments, advancing the clips further comprises advancing a pusher for advancing the clips, where a portion of the pusher is alternately flexible for bending into a coil configuration allowing it to be stored in the handle, and alternately straight and rigid for advancing the clips in the sleeve.

In some embodiments, the method further comprises one or more ratchets for engaging the pusher to control the advancement of the pusher from the coil configuration to the straight rigid pusher for advancing the clips.

In some embodiments, the method further comprises rotating a dial provided with the handle to rotate the clips housed in the sleeve in synchrony with a rotation of the sleeve, where a ball and socket joint provided with the pusher enables the handle to remain stationary relative to the rotated clips.

In some embodiments, the sleeve houses the interconnected clips with a pair of clip arms of the interconnected clips oriented lengthwise along a length of the sleeve.

In some embodiments, the sleeve houses the interconnected clip that are made of superelastic material.

In some embodiments, an axial distance between the exposed clip and the handle throughout the sleeve retraction steps remains constant.

In some embodiments, a diameter of the rigid sleeve is micro-laparoscopic.

There is further provided, in accordance with an embodiment, a method for deploying a clip using a micro-laparoscopic clip applier, the method comprising: positioning a clip applier to deploy a surgical clip from a rigid sleeve housing multiple ones of the surgical clips, where a pair of clip arms of the clips are oriented lengthwise along a length of the sleeve, and deploying the multiple clips from a distal end of the sleeve via a perforation made by a needle that is disposed at the distal end of the sleeve.

In some embodiments deploying the clip from the distal end of the sleeve via a perforation made by a needle comprises deploying via a Veress needle.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIG. 2F illustrates another exemplary clip for deploying using the system of FIGS. 1A-C, in accordance with an embodiment of the invention;

FIGS. 3A-C, taken together, illustrate a system for locking a clip onto tissue, in accordance with an embodiment of the invention;

FIGS. 4A-D, taken together, illustrate a handle for controlling the deployment of a clip, in accordance with an embodiment of the invention;

FIGS. 7B-D, taken together, illustrate an exemplary deployment of the clip illustrated in FIG. 7A in accordance with another embodiment of the invention.

DETAILED DESCRIPTION

Figures 1A, 1B:
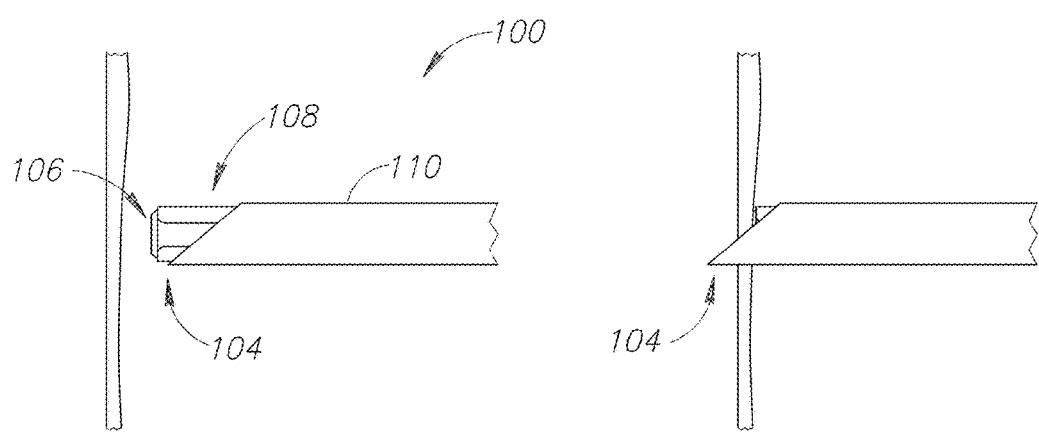
FIG. 1A-C, taken together, illustrate different stages of a micro-laparoscopic clip application system, in accordance with an embodiment of the invention.

An illustrative embodiment of the present invention relates to a micro-laparoscopic clip applier and method of use, where micro-laparoscopy typically, though not always, refers to the use of tools with a diameter of between 2 to 3 mm, or less, and a micro-laparoscopic device is a device whose sleeve is approximately 3 mm in diameter or less. Minimizing the size of the instruments for applying surgical clips, and reducing them to less than 3 mm is desirable in order to reduce the size of the incisions on the abdominal wall, and the accompanying side effects and complications. These instruments may be introduced percutaneously, piercing the abdominal wall, or other cavity wall such as the thoracic cavity, without the need of a trocar. In that case the size of the puncture is even smaller and it retracts after removing the instrument.

In general, the micro-laparoscopic clip applier includes multiple surgical clips with a micro-laparoscopic delivery system for deploying the clips onto tissue without requiring surgical incision, thus incurring less pain for the patient, fast clinical recovery and better cosmesis. The clip applier may be introduced percutaneously into a cavity, such as but not limited to the abdominal cavity, or thoracic cavity, to name a few. Although the system is particularly described for use in methods for micro-laparoscopic clip application, it will be understood that the invention is not so limited and can be used in other laparoscopic application contexts. Although the systems and method described below refer to micro-laparoscopic clip application, they are equally applicable to laparoscopic clip application, and thus any reference to micro-laparoscopic clip application may be understood to be equally relevant to laparoscopic clip application.

FIGS. 1 through 8, wherein like parts are designated by like reference numerals throughout, illustrate a micro-laparoscopic clip applier and a method of use according to the present invention. Although the present invention will be described with reference to the figures, it should be understood that many alternative forms can embody the present invention. One of ordinary skill in the art will additionally appreciate different ways to alter the parameters disclosed, such as the size, shape, or type of elements or materials, in a manner still in keeping with the spirit and scope of the present invention.

Figure 1C:
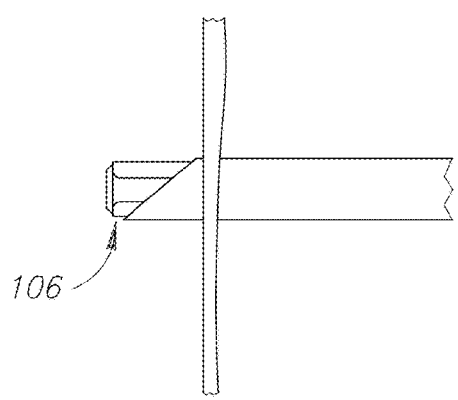

Reference is now made FIGS. 1A-C, which, taken together, show a simplified illustration of a system for micro-laparoscopic clip application, operative in accordance with an embodiment of the invention. In the system of FIG. 1A, a micro-laparoscopic clip applier 100 may be disposed with one or more surgical clips 102 (not shown). A more detailed description of clips 102 is given below with respect to FIGS. 2 and 3A-B.

Clip applier 100 may be disposed with a needle mechanism for applying multiple clips 102 percutaneously via a combined deployment of a sharpened tip 104 that is suitable for piercing through a body cavity wall and a blunt tip 106, which may comprise a distal end of any of clips 102. For example, the distal end of applier 100 may comprise a Veress needle.

Clip applier 100 may be disposed with an optionally stiff, or rigid inner sleeve 108 with a blunt distal end for housing multiple clips 102. The clips housed in sleeve 108 may have their arms oriented lengthwise along the length of the sleeve, and the distal end of the most distally positioned clip 102 housed in sleeve 108 may form blunt tip 106. Sharp tip 104 may form a distal end of an outer sleeve 110 encasing inner sleeve 108 and providing a needle to applier 100. Sharp tip 104 and blunt tip 106 may move in relation to each other, such as by moving inner and outer sleeves 108 and 110, thereby alternately exposing or recessing sharp tip 104 and blunt tip 106.

The following example describes deploying a surgical clip via a Veress needle configuration, as known in the art. Referring to FIG. 1A, when the distal end of system 100 is situated outside a body cavity wall 112, a spring (not shown) connecting the inner and outer sleeves 108 and 110 biases blunt tip 106 coupled with inner sleeve 108 to protrude, and sharp tip 104 integrated with the outer sleeve 110 to be recessed.

Referring to FIG. 1B, upon pressing the needle against a wall of a body cavity, the tissue wall pushes blunt tip 106 backwards causing blunt tip 106 to recess, exposing sharp tip 104, thereby enabling penetration of the body cavity wall.

Referring to FIG. 1C, after penetrating the body cavity wall, the spring may bias the blunt tip 106 to protrude beyond sharp tip 104 to protect any adjacent organs from injury. In this manner, clip 102 is deployed from the distal end of the sleeve housing it, via a perforation made by sharp tip 104, enabling a controlled and safe application of clip 102 in the body cavity, which will be described in greater detail below.

Alternatively, the advancement and retraction of tips 104 and 106 may be controlled by an operator.

The following steps describe an exemplary method for deploying a clip percutaneously using the system of FIGS. 1A-C, in accordance with an embodiment of the invention. A needle disposed with a sharp tip, a blunt tip, and surgical clips may be pressed against a wall of a body cavity. The blunt tip may be pushed back by the body cavity wall, thereby recessing the blunt tip and exposing the sharp tip. The body cavity wall may be penetrated by the sharp tip. After penetration, a spring coupled with the sharp and blunt tips may release and push the blunt tip forward, past the sharp tip, thereby protecting the surrounding tissue from the sharp tip. The clip may be advanced from the blunt tip and deployed, such as by applying the method described below, thereby ligating a tissue, such as a blood vessel, with the clip.

Figure 2A:
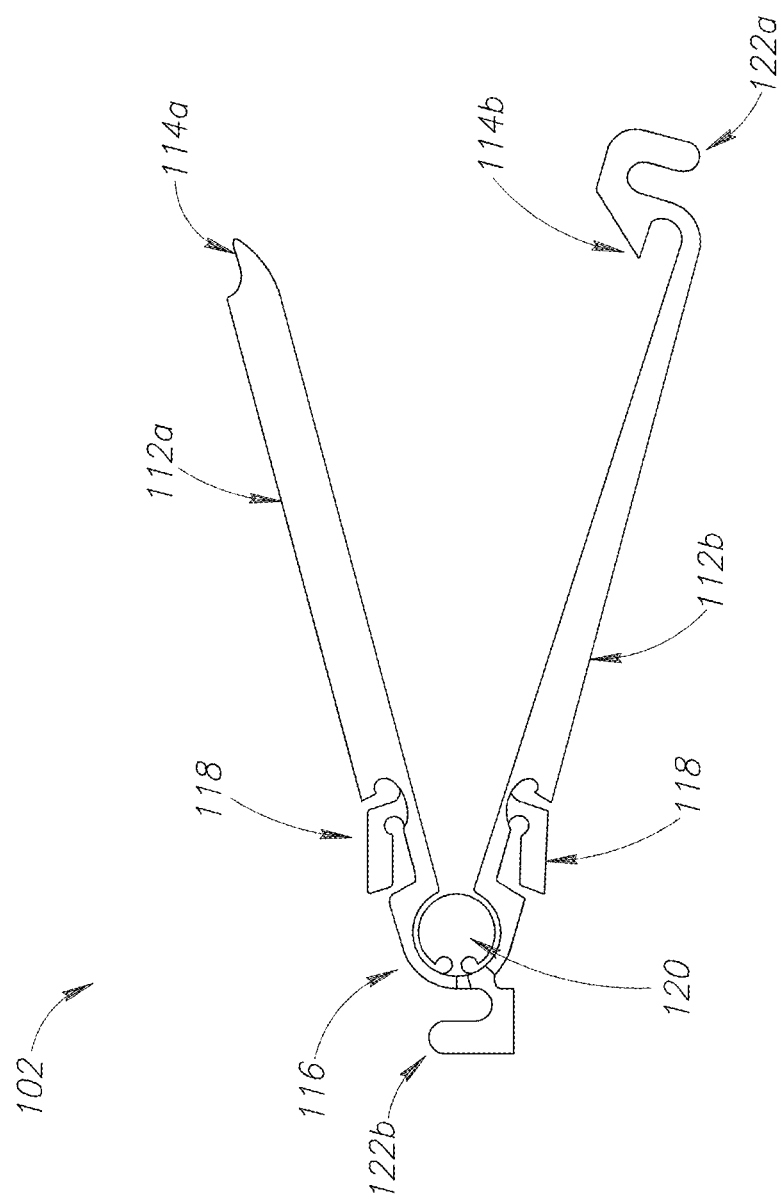
FIG. 2A illustrates an exemplary clip for deploying using the system of FIGS. 1A-C, in accordance with an embodiment of the invention.

Reference is now made to FIG. 2A which illustrates a clip 102 operative with an embodiment of the invention. Clip 102 may be made from any suitable material, such as stainless steel, titanium, or regular Nitinol, plastic, elastic or a biodegradable material. In some embodiments the clips are made at least partially of superelastic material. In some embodiments, the length of clip 102 may range from 2 mm to 30 mm long, and optionally range from 5 mm to 20 mm long. In some embodiments the clip diameter may be less than 1 mm. In some embodiments the clip diameter may be less than 2 mm. In some embodiments the clip diameter may be less than 3 mm. In some embodiment, system 100 may house approximately 20 clips, in other embodiment system 100 may house between 10 and 20 clips, or between 5 to 10 clips. Clips 102 may apply a force of at least 1N when ligating a bodily tissue. In another embodiment, the effective length for compressing the ligated tissue may be at least 70% of the length of the clip.

Clip 102 may be disposed with arms 112a and 112b that are configured to ligate bodily tissue, such as a blood vessel, via locking units 114a and 114b positioned at the distal ends of arms 112a and 112b and forming locking mechanism 114. For example, locking units 114a and 114b may provide a one-way locking mechanism with a squeezable arm-to-arm locking mechanism that provides a protrusion on one arm for matching to a groove or recess provided on the other arm. Alternatively, the clip locking mechanism may include a protrusion engaging a recess or hole on the proximal end of the clip when compressed, or a ring which is pushed forward over the arms causing them to approximate and compress the tissue.

Arms 112a and 112b may be configured in a variety of forms to suit a specific functionality. For example the clip arms may be disposed with one or more serrations, teeth or roughened surface on the surface that make contact with the tissue to improve tissue grasping and ligation; alternatively the arms may be smooth; the arms may be curved and have an arc shape when clamped, alternatively, they may be straight.

Clip arms 112a and 112b may be connected by a hinge, such as an integrally-formed hinge 116 that is configured to bias arms 112a and 112b to open upon being advanced out from sleeve 108. Clip 102 may be disposed with one or more flexible or springy prongs 118 that branch from arms 112a and 112b for applying a moment to close the clips and activate the clip locking mechanism. Advantageously, prongs 118 are configured to lie parallel to arms 112a and 112b, thereby allowing clips 102 to advance smoothly within sleeve 108. Upon advancing and exposing clip 102 from the distal end of sleeve 108, hinge 116 may bias arms 112a and 112b open, causing prongs 118 to radiate outwards from arms 112a and 112b to enable closing and locking clip 102, which will be described in greater detail below. Clip 102 may provide a barrier 120, such as a ring, for blocking tissue from entering into hinge 116. Additionally, barrier 120 may provide lateral stability to arms 112a and 112b, reducing sideways moment and providing increased control for deploying clip 102.

Clip 102 may be further provided with an interconnecting mechanism 122 for interconnecting clips 102 housed in sleeve 108. Mechanism 122 may comprise a distally positioned 'head' 122a disposed with a proximal clip for connecting to a proximally positioned 'tail' 122b disposed with a distal clip, thereby connecting the clips housed in sleeve 108. Interconnected clips 102 may be advanced within sleeve 108 by a pusher which will be described in greater detail below. For example, in one embodiment head 122a and tail 122b may be hooks configured to interconnect in a 'handshake' configuration. In one embodiment, head 122a of the most distally positioned clip in sleeve 108 may form blunt tip 106. Upon deployment, distal clip 102a may be disconnected from the subsequent clip 102b positioned directly proximal to by releasing the interconnection mechanism 122 connecting the two clips, such as by shifting sleeve 108 sideways to release tail 122b of the deployed clip from head 122a of the subsequent clip.

In this manner, multiple interconnected clips 102 may be housed in sleeve 108 for deployment by arranging the clips sequentially with clip arms 112a and 112b oriented lengthwise along the length of sleeve 108 and engaging tail 122b of a distally positioned clip with head 122a of a proximally positioned clip. In this manner, advancing a proximally positioned clip may advance the remaining clips in the sleeve, and position a most distally positioned clip for deployment.

Interconnecting mechanism 122 may fit snugly within sleeve 108, preventing lateral displacement of the clips 102.

Clips 102 may be housed within inner sleeve 108 in a manner that enables clips 102 to be stored in close proximity to each other, while preventing clip arms 112a and 112b from locking. For example, contact between the arms may be prevented by configuring inner sleeve 108 with a diameter large enough to accommodate clips 102 without applying pressure on clip locking mechanism 114. Additionally one or more slender rods, wires or strips (not shown) may be provided to interpose between the clip arms within inner sleeve 108 to prevent the arms from locking. In one embodiment, inner sleeve 108 may have a diameter which is sufficiently large to house clip 102 in a manner that prohibits locking of clip 102 within the inner sleeve 108, such as a diameter ranging between 0.2 mm and 5 mm, and optionally between 1 mm and 2.5 mm.

Figure 2B:
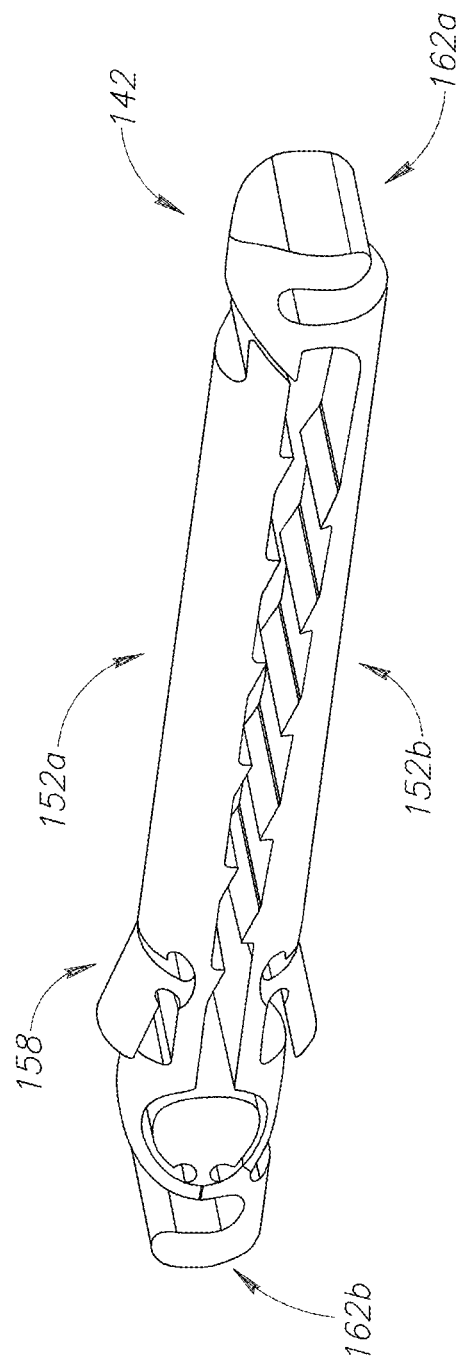
FIG. 2B illustrates another exemplary clip for deploying using the system of FIGS. 1A-C, in accordance with an embodiment of the invention.

Reference is now made to FIG. 2B which illustrates an isometric view of a clip 142 operative with another embodiment of the invention. Clip 142 may be substantially similar to clip 102 with the noted trait that clip 142 may be provided with a rounded geometry, such as a circular cross-section, thus improving the fit of clip 142 within cylindrical sleeve 108 and which may reduce wiggle room and prevent the clip from twisting out of alignment. Arms 152a and 152b and prongs 158, corresponding to arms 112a and 112b and prongs 118, may provide a semi-circular cross-section so that when arms 112a and 112b are closed and prongs 158 are compressed, such as when clip 142 is positioned within sleeve 108 prior to deployment, clip 142 is dispose with a cylindrical shape for fitting within cylindrical sleeve 108. Similarly, head 162a forming blunt tip 162a, optionally engaged with tail 162b, corresponding to head 122a, tail 122b, and tip 106 above, may provide a circular cross-section enabling a smooth transition within cylindrical sleeve 108 and reducing possibilities for misalignment within the sleeve.

Figure 2C:
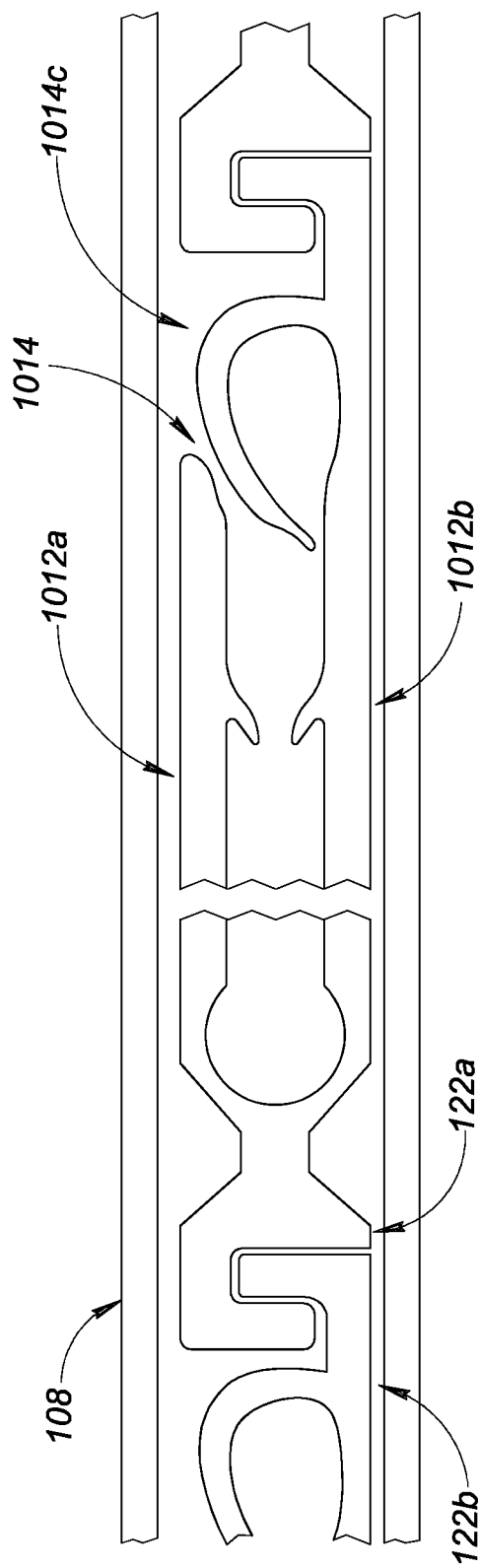
FIGS. 2C-E illustrate another exemplary clip for deploying using the system of FIGS. 1A-C, in accordance with an embodiment of the invention.
Figure 2D:
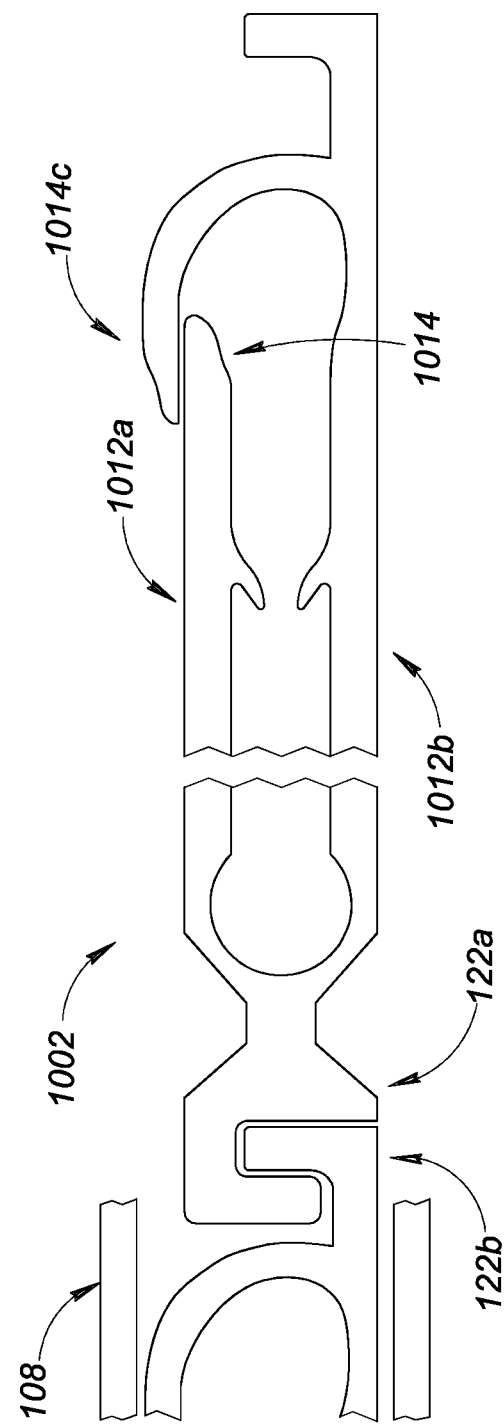

Reference is now made to FIGS. 2C-D which, taken together, illustrate another clip operative with an embodiment of the invention. A clip 1002, similar to clip 102 above may be disposed with a locking mechanism 1014 comprising an elastic hook, or prong, 1014c disposed at the distal end of arm 1012b for catching arm 1012a to lock clip 1002, thereby activating the locking mechanism of the clip. Hook 1014c, normally biased outwards, may be compressed to lie tucked, or folded inwards between arms 1012a and 1012b while clip 1002 is housed within sleeve 108, preventing the clips from locking prior to deployment and enable their smooth advancement within sleeve 108. Upon advancing and exposing clip 1002 from the distal end of sleeve 108, proximal hinge 116 connecting clip arms 1012a and 1012b may bias the arms open. Additionally, elastic hook 1014c may protrude outwards from arm 112b in a manner that allows hook 1014c to catch arm 1012a as the clip arms close.

The length of elastic hook 1014c may be greater than the inner diameter of sleeve 108, and may overlap slightly with arm 1012a so that pushing the clip arm 1012a towards clip arm 1012b, such as by advancing sleeve 108 over the clip arms, engages the distal end of arm 1012a with hook 1014c, thereby locking the clip.

Figure 2E:
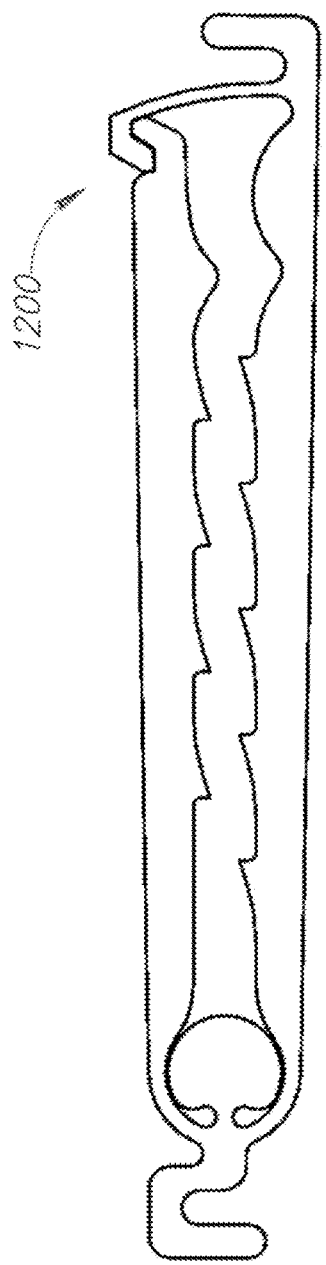

In one embodiment, Hook 1014c may engage arm 1012a in a latch-type, or geometric interlocking configuration 1200, requiring a greater force for unlocking clip 1002 than for locking clip 1002, as illustrated in FIG. 2E.

In this manner, the clip may be housed within sleeve 108 in an unlocked position, and may be closed and locked during deployment without necessitating a differential moment provided by prongs or other mechanisms. Furthermore, the length of hook 1014c may allow clip arms 1012a and 1012b to close and lock while not lying completely parallel to each other. For example clip arms may provide a small gap between the arms and may span a small non-zero angle when closed and locked with hook 1014c.

Figure 3A:
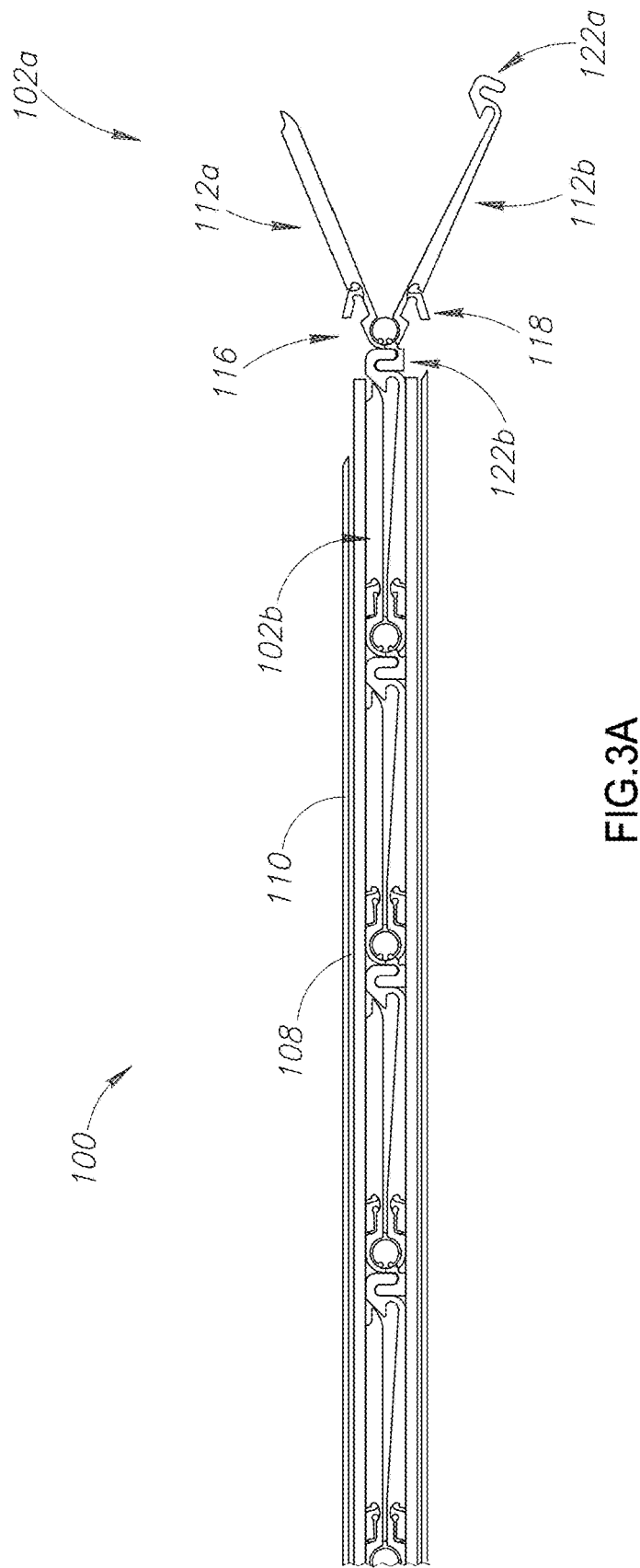

Reference is now made to FIG. 3A-C which, taken together, illustrate an exemplary deployment of the clips described above by applier 100, operative with an embodiment of the invention. The description below refers to clips 102 for exemplary reasons only, however the description of FIGS. 3A-C equally applies to deploying any of the clips described herein.

Referring to FIG. 3A, clip 102a is shown in an open position after advancing out of applier 100, details of the advancement mechanism will be described in greater detail below with respect to FIGS. 4A-C, 5A-B, and 6A-C. While housed within inner sleeve 108, prongs 118 may be compressed to radially align with arms 112a and 112b so as not to protrude from the arms, enabling a smooth advancement of clips 102 in sleeve 108. Upon advancing clips 102 forward towards the distal end of sleeve 108, the most distally positioned clip 102 may be positioned for deployment by exposing at least a portion of the clip from the distal end of sleeve 108, such as exposing arms 112a and 112b and hinge 116, causing arms 112a and 112b to open. The elasticity of prongs 118 may bias the proximal ends of prongs 118 to protrude radially outwards from arms 112a and 112b. As a result, a wider angle may be spanned by the proximal ends of prongs 118 than the angle spanned by arms 112a and 112b.

Referring to FIG. 3B, inner sleeve 108 may be moved relative to the clip positioned at the distal end of sleeve 108, such as by advancing sleeve 108 over clip arms 112a and 112b to push against the protruded prongs, thereby applying a moment by prongs to push the clip arms together so that the clip arms lie substantially parallel to each other and close over a bodily tissue. Inner sleeve 108 may be disposed with a contoured distal end to allow sleeve 108 to advance over arms 112a and 112b without pinching the tissue positioned within the clip arms 112a and 112b, such as by disposing sleeve 108 with hollowed side walls, or carved out slots at the distal tip.

Further moving the inner sleeve forward relative to the positioned clip may further push the distal end of inner sleeve 108 against the proximal ends of prongs 118, pushing the distal end of prongs 118 against arms 112a and 112b thereby applying a moment that pushes arms 112a and 112b together and result their engagement at their distal tip by engagement of locking means 114a and 114b, as illustrated in FIG. 3C.

It may be noted that upon advancing the clips to expose and position the most distally positioned clip at the distal end of the sleeve for deployment, the axial distance of the exposed clip with respect to the bodily tissue as well as to the clip applier is unchanged throughout the closing and locking steps. This is achieved by moving sleeve 108 relative to the positioned clip while keeping the clip axially stationary. Furthermore, the sleeve and clip interconnecting means, which will be described in greater detail below, provide radial stability during deployment to maintain a steady radial orientation of the clip throughout the clip closing and locking steps.

The differential height, or angle spanned by the proximal ends of prongs 118 provides the differential moment required for sleeve 108 to lock arms 112a and 112b together over the tissue and engage locking units 114a and 114b.

Clips 102 may be advanced in sleeve 108 via any suitable advancement technique. An exemplary advancement technique is described in greater detail below.

Reference is now made to FIG. 2F which illustrates a surgical clip in accordance with another embodiment of the invention. Clip 172 may be substantially similar to clips 102 and 142 above with the notable difference that, in place of prongs 118, clip 172 may be disposed with niches 188 at the proximal end of arms 182a and 182b, corresponding to arms 112a and 112b, respectively. The deployment of clips 172 may be similar to the deployment of clips 102 described above with respect to FIGS. 3A-C with the notable different that sleeve 178, corresponding to sleeve 108, may be disposed at the distal end with flexible sleeve prongs 178a for engaging with niches 188 as clip 172 advances from the distal end of sleeve 178. Prongs 178a may apply a moment to close the clips and activate the self locking mechanism of the clip. Prongs 178a may be biased radially inwards to engage with niches 188 but may be sufficiently flexible so as not to exert pressure on arms 182 and 182b as clip advances from the distal end of sleeve 178. In this manner, clip arms 182*a* and 182*b* may be exposed from sleeve 178 without engaging locking mechanism 184, corresponding to mechanism 114 above.

Upon advancing clips 172 distally in sleeve 178, hinge 176 of the most distally positioned clip 172 in sleeve 178 may be exposed from sleeve 178, biasing arms 182*a* and 182*b* to open. The elasticity of prongs 188 provided at the distal end of inner sleeve, may bias the distal ends of prongs 188 to protrude radially inwards toward arms 182*a* and 182*b* and engage with niches 178*a*. The advancement of inner sleeve 178 may push the distal ends of prongs 188 of inner sleeve 178 against niches 178*a*, provided on arms 182*a* and 182*b*, thereby applying a moment that pushes arms 182*a* and 182*b* together and result in their engagement at their distal tip by engagement of locking means 184*a* and 184*b*, as illustrated in FIG. 2C.

In one embodiment, prongs 188, may be wider proximally than distally and may be provided with a groove for engaging the corresponding clip arm in order to support the clip and prevent any radial misalignment of the clip while the sleeve is moved relative to the clip during deployment.

Clips 172 may be advanced in sleeve 178 via any suitable advancement technique. An exemplary advancement technique is described in greater detail below. Advantageously, the inward protrusion of the prongs provided at the distal end of inner sleeve and that engage reciprocal recessions on the clip arms, provides the differential moment required to lock arms 182*a* and 182*b* 172*b* together over the tissue and engage locking units 184*a* and 184*b*.

The following steps describe an exemplar method for deploying a clip percutaneously using the system of FIGS. 3A-C, in accordance with an embodiment of the invention. A clip disposed with springy prongs branching from the clip arms is housed in a sleeve with the prongs compressed to align radially with the arms, thereby allowing the clip to advance smoothly within the sleeve. The clip is advanced from the sleeve exposing the prongs from the sleeve. The clip hinge is exposed from the sleeve, and the clip arms are opened. The springy prongs extend outwards and protrude from the arms, thereby providing a wider angle spanned by the prongs than by the clip arms. The sleeve is advanced, and the distal end of the sleeve is pushed initially against the clip arms closing them on tissue by the moment applied, and then the end of the sleeve is pushed against the proximal end of the prongs. The additional moment is applied by the prongs to the clip arms. The clip arms are locked by engaging a locking mechanism disposed at the distal end of the clip, and the tissue is ligated.

Referring back to FIG. 3A, interconnecting mechanism 122 comprising distally positioned 'head' 122*a* and proximally positioned 'tail' 122*b* may enable advancement of clips 102 within sleeve 108 for deployment, by each clip pushing the next one. A proximal pusher that is interconnected with the most proximal clip, is used to advance the most proximal clip by pushing it. For example, in one embodiment head 122*a* and tail 122*b* may be hooks configured to interconnect in a 'handshake' configuration. When positioned distally, head 122*a* may form blunt tip 106. The interconnecting head of distal clip and tail of proximal clip representing the handshake region is situated within the lumen of the surrounding sleeve and fits snugly within it during clip opening, closing and locking on tissue. Therefore, this clip tail 122*b* will be firmly held during deployment preventing rotation or displacement. After locking the clip on tissue the sleeve is retracted exposing the handshake region and the distal clip 102*a* may be unlocked from the previous clip 102*b* positioned directly proximal to it by shifting sleeve 108 sideways in a manner to unlock tail 122*b* of the deployed clip from head 122*a* of the subsequent clip. Advantageously, sleeve 108 is configured to be sideways maneuverable in a manner that does not alter the positioning clip 102. Interconnecting clips 102 via interconnecting mechanism 122 may allow for simple and easy deployment of multiple clips 102 stored in sleeve 108, allowing the operator to control the advancement of the clips in sleeve 108 by controlling the motion of the most proximally positioned clip, and which will be described in greater detail below.

The following steps describe an exemplar method for advancing a clip for deployment, using the system of FIGS. 3A-B, in accordance with an embodiment of the invention. Multiple clips may be provided for deployment by positioning the clips in a sleeve disposed with a needle at the distal end. The clips may include an interconnecting mechanism, such as by providing a head at the distal end of the clip that is configured to interconnect with a tail provided at the proximal end of the clip. The clips may be arranged sequentially in the sleeve by engaging the tail of a distally positioned clip with the head of a proximally positioned clip, thereby interconnecting the clips.

Reference is now made to FIGS. 4A-D which, taken together, illustrate an exemplary system for controlling the deployment of the interconnected clips housed in the inner sleeve, in accordance with an embodiment of the invention. Although the description below refers to clip 102, this is for exemplary purposes only, and the description may be similarly applicable for the deployment of any of the clips described herein, with any differences noted below.

Applier 100 may provide a handle 430 for operating a deployment mechanism included with handle 430 for deploying any of the clips described above.

Sleeves 108 and 110 may extend from handle 430 allowing the deployment mechanism to deploy the clips housed in inner sleeve 108 via a perforation in a body cavity wall made using sharp tip 104 provided with the distal end of outer sleeve 110 of the Veress needle.

Handle 430 may include a mechanism for maneuvering sleeve 108 with respect to the clips housed in the sleeve. The sleeve maneuvering mechanism may include a trigger 432, extending from handle 430, for moving inner sleeve 108, to deploy any of the clips described above. Trigger 432 may connect to inner sleeve 108 via a hinge 434 and spring 436 that may translate retrograde motion by trigger 432, such as by the operator, to compress spring 436 and advance sleeve 108 forward and push prongs 118 or 158 for locking clip 102 or 142, respectively, in accordance with the method described above. Releasing trigger 432 may release spring 436 via hinge 434, and return sleeve 108 to its former position.

Handle 430 may similarly be applied to deploy clip 172 with the notable difference that advancing sleeve 178 forward over clip 102 may cause pr//ongs 188, disposed at the distal end of sleeve 178, to engage with niches 178*a*, disposed on clip arms 182*a* and 182*b*, thereby applying a moment for closing and locking clip arms 182*a* and 182*b*.

Reference is now made to FIGS. 4A-D, which illustrate an exemplary deployment of clip 102 using handle 430. The most distally positioned clip 102 housed in sleeve 108 may be exposed from the distal end of sleeve and positioned for deployment via any suitable clip advancement method. An exemplary clip advancement method is described in greater detail below.

Referring to FIG. 4A, while trigger 432 may be in an initial position, inner sleeve 108 may be in a recessed position and arms 112a and 112b of clip 102 may be open.

Figure 4B:
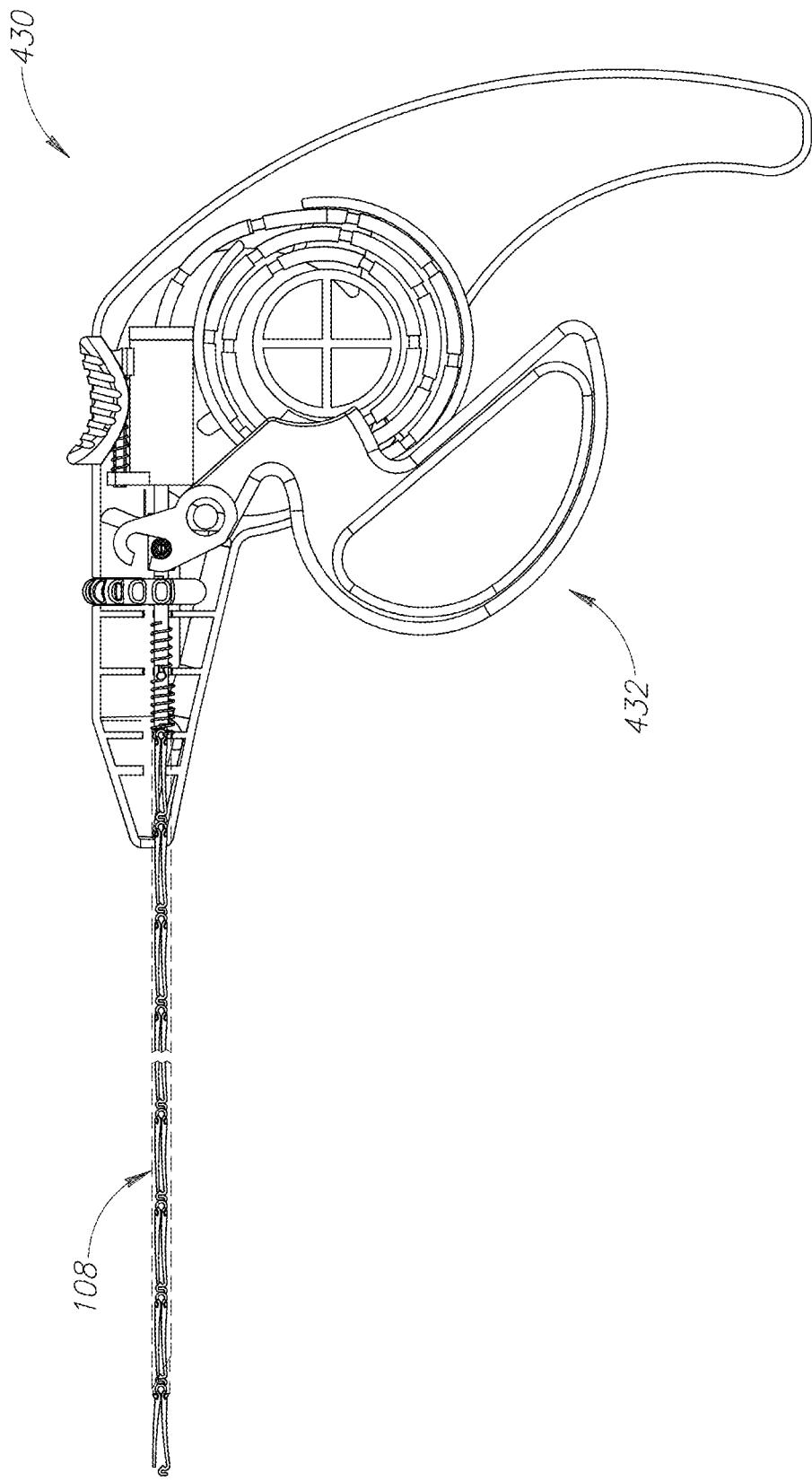

Referring to FIG. 4B, trigger 432 may be squeezed, or pushed proximally with respect to clip 102, and hinge 434 may translate the proximal motion of trigger 432 to at least partially compress spring 436 and push sleeve 108 distally, advancing sleeve 108 forward with respect to exposed clip 102 to press against prongs 118 which apply a moment to close clip arms 112a and 112b, as described above.

Figure 4C:
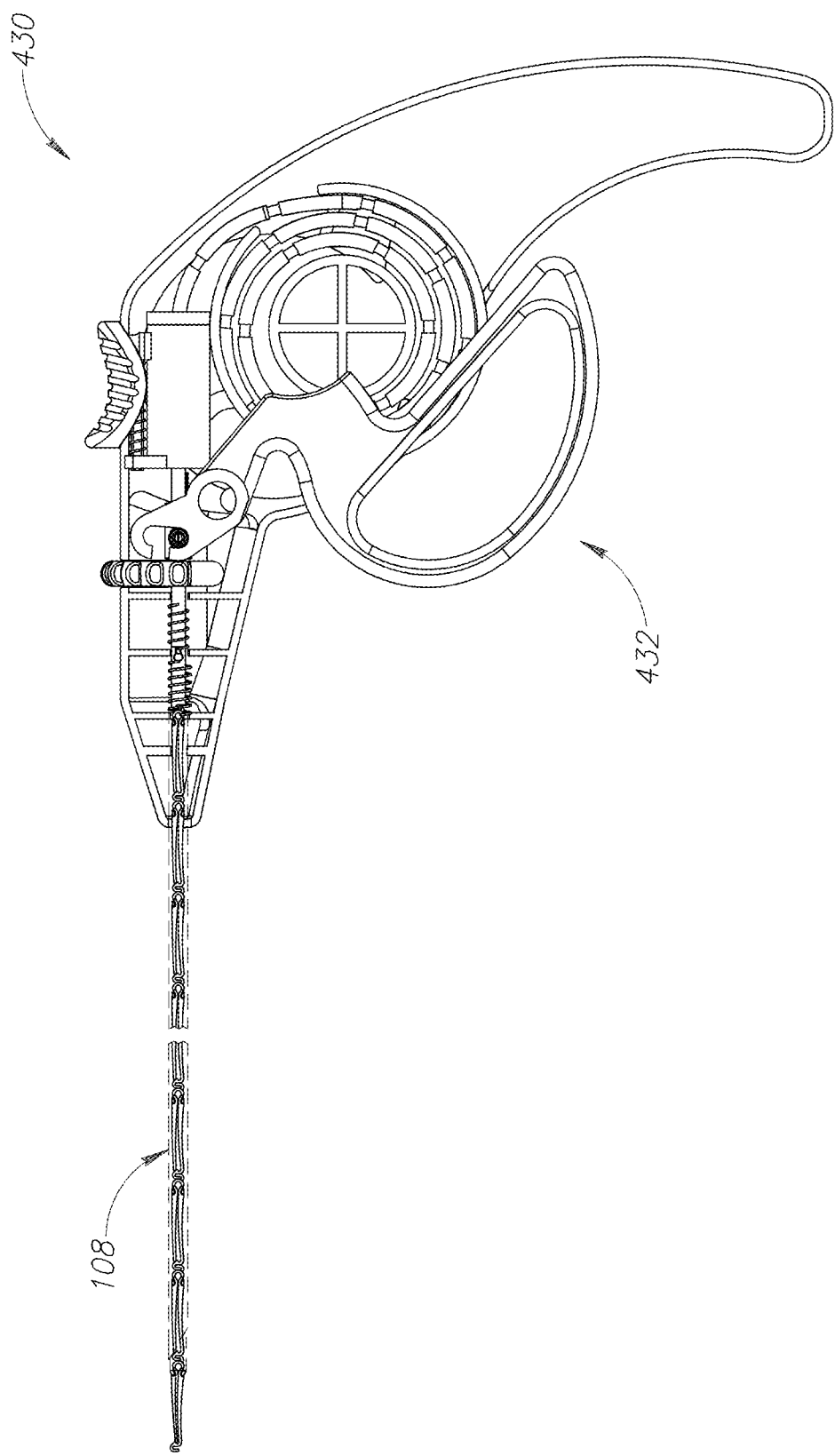

Referring to FIG. 4C, trigger 432 may be further pressed proximally, thereby further compressing spring 436 via hinge 434 to further advance sleeve 108 with respect to the exposed clip and press against prongs 118 to apply a moment thereby locking clip 102 via mechanism 114.

Figure 4D:
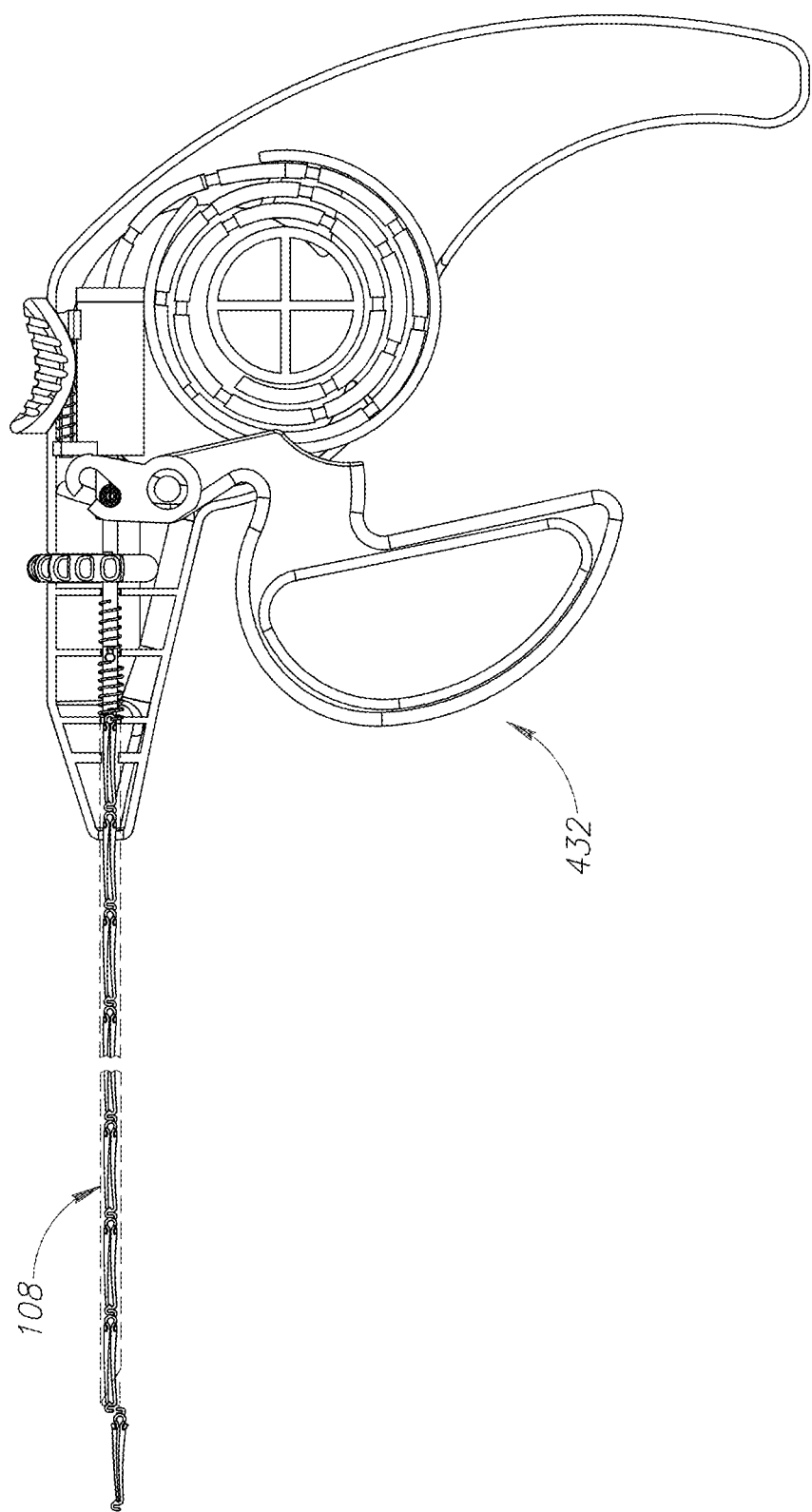

Referring to FIG. 4D, releasing trigger 432 may release spring 436 which may push trigger 432 distally and pull sleeve 108 proximally to retract the sleeve with respect to the deployed clip, such as to almost reach the distal end of outer sleeve 110. Interconnecting mechanism 122 may be exposed from the distal end of sleeve 108, and the deployed clip 102 may be released from the next most distally positioned clip 102 housed in sleeve 108 by disengaging interconnecting head 122a from tail 122b, such as by having the operator shift handle 430 sideways to release the interlocking mechanism.

It may be noted that upon positioning any of the above clips for deployment at the distal end of the inner sleeve, the axial distance between the positioned clip and the handle remains constant throughout the sleeve moving, clip closing and clip locking steps. By moving the sleeve relative to the clip throughout the deployment, and maintaining the clip's axial positioning, the positioned clip isn't dislodged or misaligned during deployment. Furthermore, the axial distance from the clip to the handle, and therefore, the operator is kept constant. In this way, the operator may accurately position the clip for deployment, and deploy the clip by maneuvering the sleeve, knowing that the position of the deployed clip will not change.

In one embodiment, sleeve 108 may be provided with lateral restricting means along a portion of its length to reduce the profile of the sleeve channel to a rectangular like shape and prevent any of the clips described above to rotate within the sleeve.

It may be noted that the handle mechanism described above is exemplary only and that other suitable methods for maneuvering sleeve 108 or 178 for deploy any of the above clips may be applied.

The following steps describe an exemplar method for advancing a clip for deployment, by operating a handle, such as the handle illustrated in FIGS. 4A-D, in accordance with an embodiment of the invention. A trigger connected to a hinge may be provided to advance the sleeve illustrated in FIGS. 3A, and 4A-C for deploying a clip. The trigger may be squeezed backwards, or proximally, activating the hinge that translates the proximal motion of the trigger to a forward or distal motion of the sleeve. In this manner, squeezing the trigger may push the sleeve forward against the clip arms to close the clip. Squeezing the trigger further pushes the sleeve further against the clip prongs to lock the clip. In this manner, by controlling the trigger, an operator may control the closing and locking of the clip.

Figure 5:
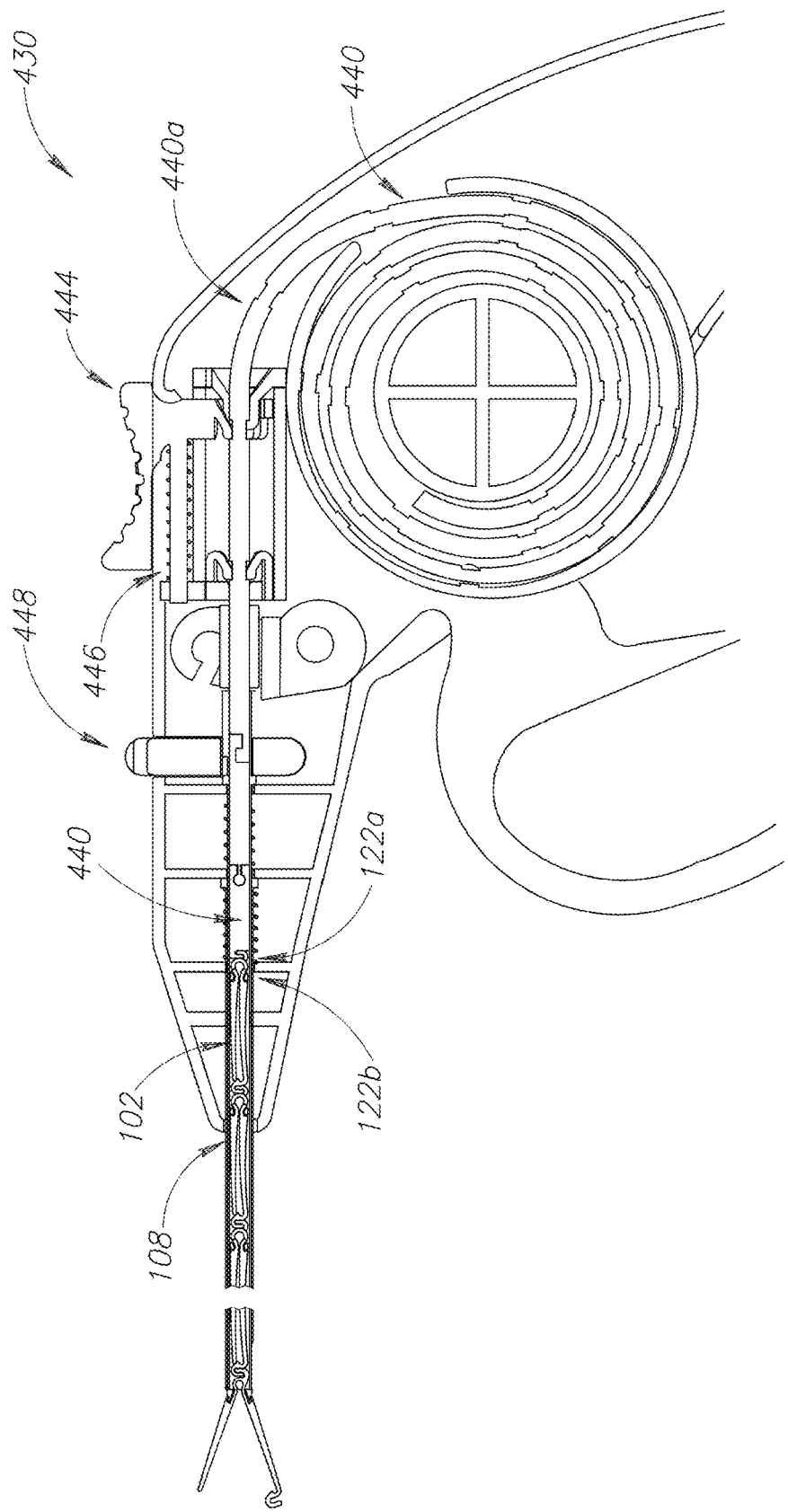
FIG. 5 illustrates another view of the handle of FIGS. 4A-D, in accordance with an embodiment of the invention.

Reference is now made to FIG. 5 which illustrates a clip advancement mechanism included with the deployment mechanism of handle 430 for advancing clips 102 for deployment in accordance with system 100 described above. Although the description below refers to clip 102, this is for exemplary purposes only, and the description may be similarly applicable for the deployment of any of the clips described above, with any differences noted below.

Handle 430 may include a pusher 440 that penetrates sleeve 108 to advance, and thereby deploy clips 102. The distal end of pusher 440 may provide an interconnecting mechanism, such as interconnecting 'head' 122a, for engaging with tail 122b of the most proximally positioned clip 102 in sleeve 108. In this manner, advancement of pusher 440 may advance interconnected clips 102 within sleeve 108, thereby deploying the clips.

In one embodiment, a proximal portion of pusher 440a may be disposed to be folded into a coil for storing within handle 430. In some embodiments, pusher 440a may be made of flexible material, such as: Nylon, Polyethylene, etc, allowing it to be stored within handle 430 in a compact manner, such as by winding pusher 440a into a coil, where the length of pusher 440a when unwound may be similar to the length of sleeve 108. Alternatively, in another embodiment, pusher 440a may be made of straight interconnected segments that are connected by integral hinges, or real hinges such as but not exclusively of a ball and socket type, allowing a portion of the pusher to be alternately flexible for bending into a coiled configuration while housed in the handle, or alternately in a straight and rigid configuration for penetrating the sleeve to advance the clips in the sleeve. In some embodiments, most of the length of the slender sleeve 108 may be exploited to house clips for deployment while the pusher 440a is coiled in a compact manner within the handle. As the clips are deployed by the operator, pusher 440a may be advanced within the sleeve 108, such as by advancing the clips one by one for subsequent deployment.

A dial 448 may be provided with handle 430 for rotating sleeve 108 together with any clips 102 housed within sleeve 108. For example, sleeve 108 may provide means for synchronizing a rotation of the clips housed within the sleeve with a rotation of the sleeve via the dial. In some embodiments, the orientation of clips 142 may be synchronized with the sleeve by virtue of their good fit within the sleeve, such as for round clip 142. Other embodiments for clips may have their orientation synchronized using a ridge or any other suitable means within the sleeve to rotate the clips together with the rotation of the sleeve.

A joint 440b, such as a ball and socket joint, may be provided with pusher 440 to connect the rigid distal portion of pusher 440 coupled to clips 102 via interconnect mechanism 122 to the alternately flexible proximal portion of pusher 440a housed within handle 430. In this manner the clips housed in sleeve 108 and connected to distal pusher 440 may rotate in synchrony with a rotation of sleeve 108 via dial 448 independently of the proximal flexible portion of pusher 440a housed in handle 430, enabling the handle to remain stationary relative to the rotating clips. Thus, the orientation of sleeve 108 and correspondingly of the clips 102 housed within the sleeve, may be controlled and manipulated via dial 448 and joint 440b in a manner that is convenient for the operator applying the clips, by not requiring a corresponding orienting of the handle. In one embodiment, dial 448 may rotate sleeve 108 by 360 degrees.

In one embodiment, pusher 440 may be configured with multiple grooves 440a, or ridges for engaging with a ratchet mechanism 442, such as comprising ratchets, or protrusions 442a, 442b, and 442c that are provided with handle 430 for controlling the movement of pusher 440. For example, the protrusions may control the advancement of the pusher from its coiled configuration within the handle to its rigid configuration for advancing the clips within the sleeve. Additionally, the protrusions may prevent retrograde motion of the clips within the sleeve.

Figure 6A:
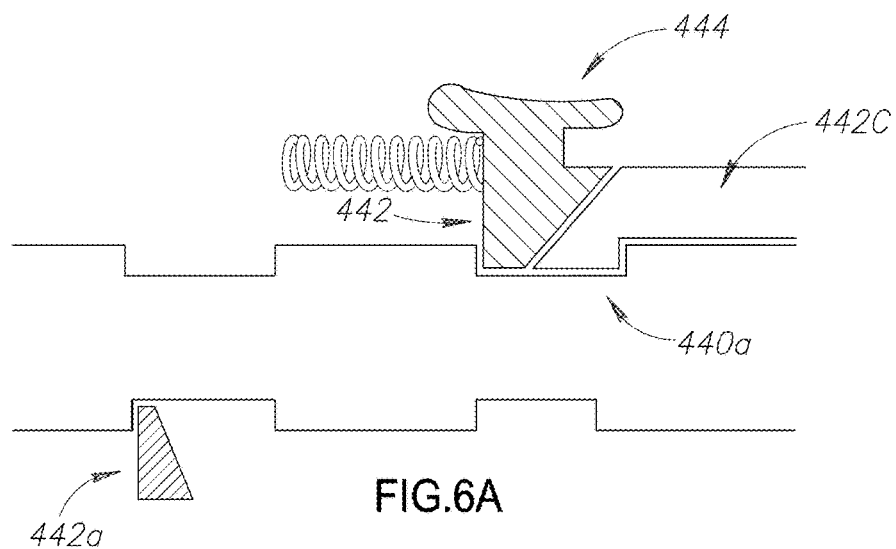
FIGS. 6A-C, taken together, illustrate another view of view of the handle of FIGS. 4A-B, in accordance with an embodiment of the invention.
Figure 6B:
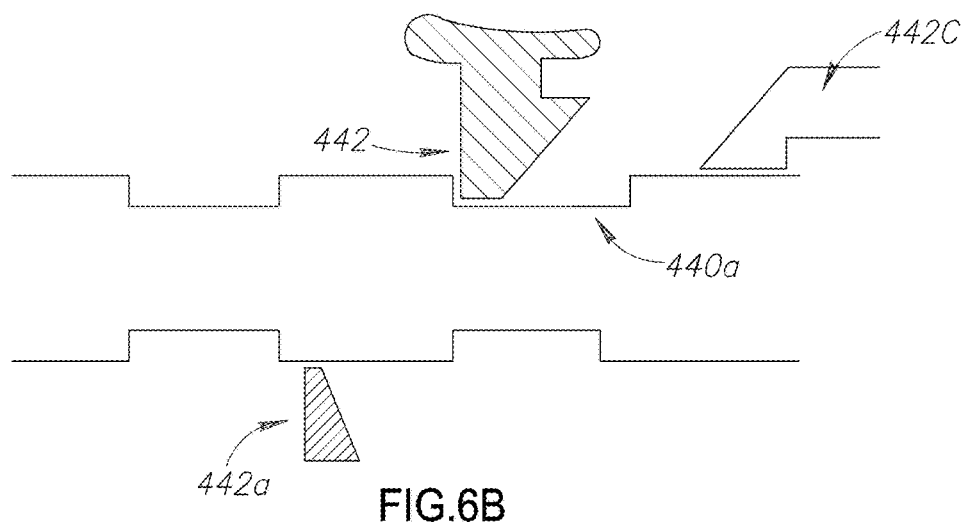
Figure 6C:
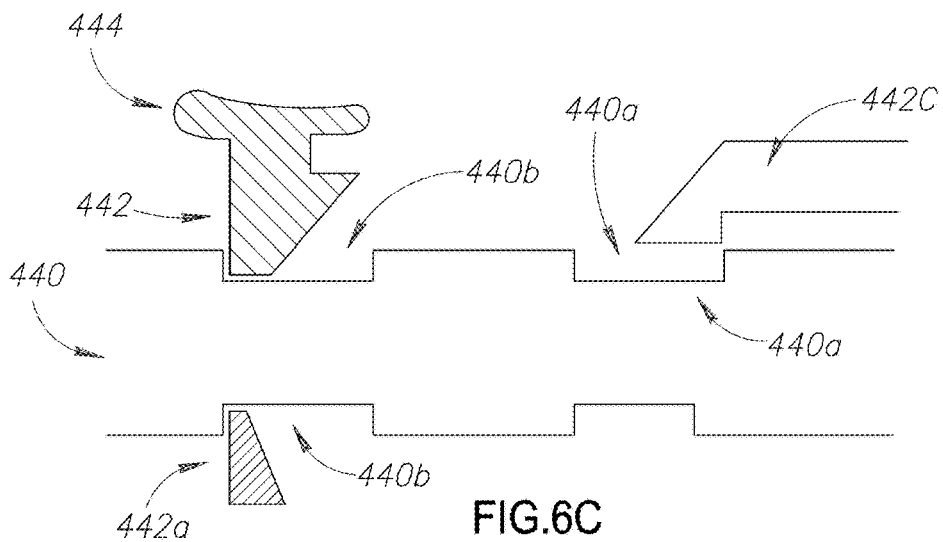

Reference is now made to FIGS. 6A-C which, taken together, illustrate an exemplary application of ratchet mechanism 442 for advancing clips 102 in sleeve 608, according to an embodiment of the invention. Ratchet 442a may be a fixed ratchet and 442b may be a moving ratchet means. These ratchet means may provide a straight angle for interfacing with the distal sides of the grooves and a gradient angle for interfacing with the proximal sides of the grooves to enable forward advancement and prevent retrograde motion of pusher 440. Similarly, ratchet means 442c may be a locking ratchet which provides a gradient angle for interfacing with the gradient angle of ratchet 442b and a straight angle for interfacing with the proximal sides of the grooves to disable forward advancement of pusher 432.

Ratchet mechanisms 442a, 442b, and 442c may be manipulated by a grip 444 coupled to a spring 446 to enabling the operator to advance pusher 540, as follows:

Referring to FIG. 6A, ratchets 442b and 442c may together engage a proximal groove 440a disposed on an overside of pusher 440, while ratchet 442a may engage with a distal groove 440b disposed with an underside side of pusher 440, where overside and underside are to be understood as relative opposite sides of pusher 440.

Referring to FIG. 6B, grip 444 may be pushed forward, causing spring 446 to compress and release ratchet 442c from its engagement with proximal groove 440a, and additionally, release ratchet 442a from its engagement with the underside groove of pusher 440. The forward motion of grip 444, attached to ratchet 442b, may pull forward pusher 440 engaged with ratchet 442b via groove 440a. In some embodiment, the distance that pusher is advanced by each activation of grip 444 is one clip length. hen spring 446 is at rest, ratchets 442a engage distal grooves 440b of pusher 440 preventing retrograde motion of pusher 440, while ratchet 442c is be biased by ratchet 442b to engage a proximal groove 440a, preventing forward motion, as illustrated in FIG. 6B. In this configuration, pusher 440 is locked, thereby preventing any advancement of the clips.

Referring to FIG. 6C, the forward motion of pusher 440 may cause fixed ratchet 442a to engage with the groove positioned on the underside of the groove engaged by ratchet 442b, while ratchet 442c may engage with the next proximally positioned groove on pusher 440. In this manner, pusher may be advanced groove by groove, where each activation of grip 444 may engage ratchets 442 from distally positioned to proximally positioned grooves of pusher 440.

Releasing grip 444 may release spring 446 and return ratchet 442b proximally by to the state illustrated in FIG. 6A, ready for the next advancement.

In this manner, an operator may maneuver grip 444 coupled to spring 446 to advance pusher 440 thereby advancing the above described clips for deployment, while ratchets 442 control the forward motion of pusher 440 to position one clip at a time for deployment, and prevent retrograde motion of the clips.

It may be noted that ratchet mechanism 442 is exemplary only and that any suitable method for controlling the advancement of the clips described above within sleeve 108 may be applied to system 100.

The following steps describe an exemplary method for advancing a clip for deployment, such as by using the system illustrated in FIGS. 5A-B and 6, in accordance with an embodiment of the invention. A pusher may be provided with the clip applier to advance the clips stored within the sleeve. The pusher may engage the proximally positioned clip in the sleeve, such as via an interconnecting mechanism similar to the mechanism connecting the clips. A grip coupled with a spring and one or more ratchets may be activated to advance the pusher forward and position a clip for deployment. A ratchet may engage a distal groove provided with the pusher to prevent retrograde motion of the pusher in an initial position of the grip. The grip may be pushed causing the spring to extend and advance the moving ratchet from the proximal groove together with the pusher forward until the pusher proximal groove is engaged by the fixed ratchet. The grip may be released, causing the spring to release backwards, bringing the moving ratchet to a more proximal grove of the pusher and making it ready for an addition step forward. The forward advancement of the pusher into the sleeve may advance the proximal clip forward into the sleeve, and thereby position the distally positioned clip in the sleeve for deployment. Advantageously, the grip, spring and ratchets are configured to advance the pusher forward by a distance equal to the length of a clip, thereby advancing the pusher into the sleeve by one clip length, and positioning the subsequent clip for deployment by activating the trigger. An additional ratchet may be provided to prevent further advancement of the pusher after a clip has been positioned for deployment.

Thus, by coordinating the advancement of the clips within the sleeve using the system illustrated in FIGS. 5A-B and 6A-C, with the closing and locking of the clip using the system illustrated in FIGS. 4A-C, the positioning and deployment of the clip may be controlled by an operator using the handle described above.

It may be noted that the above systems are illustrative only, and that any suitable mechanism for advancing the clips for deployment within the sleeve, and for engaging the locking mechanism of the clips may be applied for deploying clips 102 using system 100.

Figure 7A:
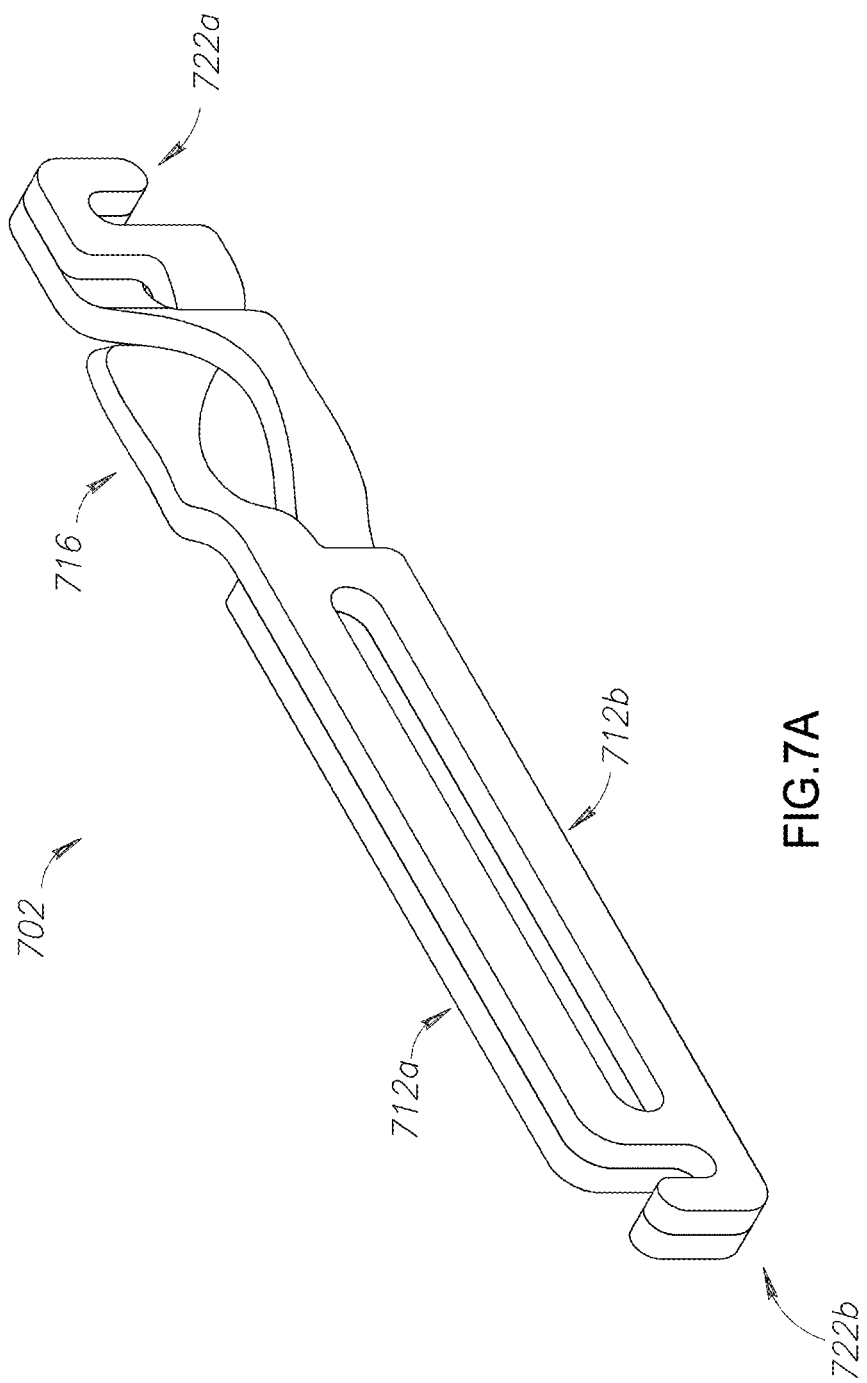
FIG. 7A illustrates an exemplary clip for deploying using the system of FIGS. 1A-C, in accordance with an embodiment of the invention.

Reference is now made to FIGS. 7A-D which, taken together, illustrate another exemplary clip for deployment via system 100, operative with an embodiment of the invention. Referring to FIG. 7A, a clip 702 may have a loop-shaped clip hinge 716, such as a spring loop, with arms 712a and 712b extending out from the distal ends of the loop with the upper arm connected to the lower end of the loop and the lower arm connected to the upper end of the loop. Clip 702 may be normally closed, such as by configuring hinge 716 to bias arms 712a and 712b closed, and to open arms 712a and 712b when compressed. Clip 702 is advantageously provided with an interconnecting head 722a and an interconnecting tail 722b that operate in a manner similar to head 122a and tail 122b described above, enabling any of interconnected clips 702 to advance through inner sleeve 708 in a similar manner to the advancement of interconnected clips 102 within sleeve 108. Clip arms 712a and 712b may be disposed with a lengthwise slit.

A handle 430A, similar to handle 430, may be provided to operate a deployment mechanism for clips 702 in a manner similar to that described for FIGS. 5A-B, and 6A-C above. Multiple interconnected clips 702 may be housed within inner sleeve 708 in their normally-closed configuration. Sleeve 708 may extend from handle 430A and may include a pusher 440 for advancing clips 702 towards the distal end of inner sleeve 708 to expose the most distally positioned clip 702 in sleeve 708 from the distal end of sleeve 708.

The distal end of pusher 440 may be disposed with a hook, such as interconnecting 'head' 722a, for engaging with a tail 722b, of the most proximally positioned clip 702 within sleeve 708. Thus, referring to FIG. 7A, by controlling the advancement of pusher 440, the operator may control the advancement of clips 702 within sleeve 708, and position clips 702 for deployment, as described above.

Handle 430A may be substantially similar to handle 430 with a notable difference that activating trigger 432 may connect to sleeve 708 via hinge 434 in a manner to cause sleeve 708 to retract, as opposed to advance, such as for clip 102. For example, hinge 434 may translate retrograde motion of trigger 432 to retrograde motion of sleeve 708, thereby pulling sleeve 708 back with respect to clip 702. In this manner, controlled activation of trigger 432 may control a retreat of sleeve 708, and deploy the clip, as follows:

At least one protrusion 724 may be provided at the distal end inner sleeve 708, corresponding to inner sleeve 108 above, for engaging with hinge 716 to compress hinge 716, thereby opening arms 712a and 712b. As shown in FIG. 7B, a clip 702 may be positioned at the distal end of a sleeve provided with a clip applier, such as by advancing the pusher using a ratchet mechanism similar to that described in FIGS. 6A-C. The arms 712a and 712b, in a normally closed configuration may protrude beyond the distal end of inner sleeve 708, while hinge 716 may be housed within sleeve 708.

Referring to FIG. 7C, sleeve 708 may be retracted with respect to the positioned clip 702 by activating trigger 432 to move sleeve 708 proximally relative to clip 702 in a first moving step. Protrusions 724 positioned at the distal end of sleeve 708 may make contact with a distal portion of clip hinge 716 and apply pressure to squeeze or compress clip hinge 716 in a manner that opens clip arms 712a and 712b.

Referring to FIG. 7D, trigger 432 coupled to hinge 434 may be further activated to retract sleeve 708 with respect to clip 702a and move sleeve 708 proximally relative to clip 702 in a second moving step that exposes clip hinge 716 from the distal end of sleeve 708 and positions protrusions 720 at the proximal end of hinge 716. This may release the pressure applied by protrusions 720 on clip hinge 716 and return clip hinge 716 to its natural state of biasing arms 712a and 712b closed.

Sleeve 708 may be moved proximally in a third retracting step with respect to the exposed clip, to expose interlocking mechanism 722 of the deployed clip from the distal end of sleeve 708, allowing the operator to disconnect the deployed clip from the remaining clips housed in sleeve 708, such as by shifting the clip applier sideways.

During the deployment stages described above, from when clip 708 is positioned for deployment at the distal end of sleeve 708, throughout the moving steps of sleeve 708 and until the clip is closed over the blood vessel, the axial distance between the clip 702 and handle 430 may remain constant. The movement of sleeve 708 throughout the deployment of clip 702 has no effect on the axial distance of the clip from the handle, and therefore, the operator. In this way, the operator may accurately position the clip for deployment, and deploy the clip by maneuvering the sleeve, knowing that the position of the deployed clip will not change.

The following steps describe an exemplary method for deploying the clip illustrated in FIGS. 7B-D, in accordance with an embodiment of the invention. A clip may be positioned at the distal end of a sleeve provided with a clip applier by advancing the pusher using a ratchet mechanism similar to that described in FIG. 6. The clip may be positioned such that the clip arms may be exposed from the distal end of the sleeve, while a hinge disposed at the proximal end of the clip is enclosed within the sleeve. The sleeve may be withdrawn in a first retreat step, such as by using a handle similar to the handle described above. One or more protrusions disposed at the distal end of the sleeve may engage with the distal side of the enclosed hinge and exert pressure on the hinge by squeezing it. The clip arms may open. The sleeve may be withdrawn in a second retreat step to position the protrusions at the proximal side of the hinge, thereby releasing the pressure from the hinge, causing the clip arms to close and lock, thereby deploying the clip. The sleeve may be withdrawn by a third retreat step to expose the hinge and an interconnecting mechanism disposed at the proximal end of the clip from the sleeve. The sleeve may be shifted in a manner to release the interconnecting mechanism, while not displacing the deployed clip. The next clip may be positioned at the distal end of a sleeve provided with a clip applier by advancing the pusher again using a ratchet mechanism similar to that described in FIG. 6.

Figure 8:
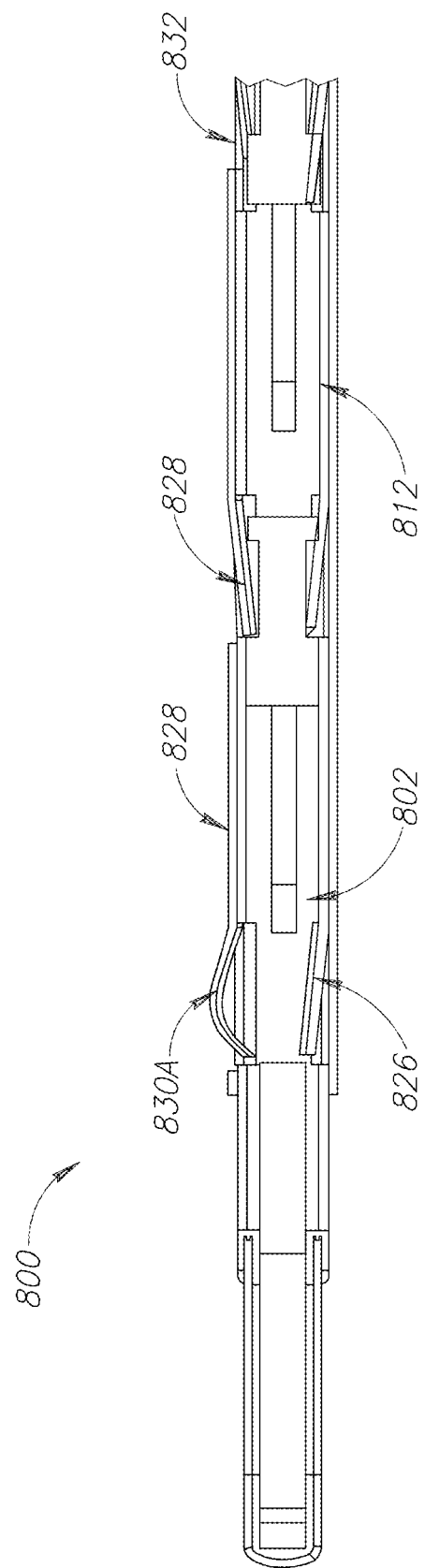
FIG. 8 illustrates a ratcheted cartridge mechanism configured to deploy one or more clips into a body cavity, operative in accordance with an embodiment of the invention.

Reference is now made to FIG. 8 which illustrates a ratcheted cartridge mechanism for advancing one or more clips for deployment into a body cavity, operative with an embodiment of the invention. In the system of FIG. 8A, a cartridge mechanism 800 configured for housing clips 802 is disposed with multiple concentric tubular structures, or sleeves, coupled with anchoring protrusions, such as ratchets, for advancing clips 802. Clips 802 are substantially similar to clips 102 with the notable difference that clips 802 are not disposed with interconnecting mechanism 122, and thus are advanced within the interconnecting sleeves using any suitable advancement mechanism, such as by using a ratcheted advancement mechanism described below.

A handle mechanism similar to handle 430 may be provided with system 800 for deploying clips 802, in a manner similar to the deployment of clips 102 by maneuvering one or more sleeves provided to house and deploy clips 802 and which are described below. The sleeves may be maneuvered by a trigger mechanism, similar to trigger 432.

Innermost sleeve 808, corresponding to inner sleeve 112 of FIG. 1A, may house multiple clips 802 in a manner similar to that described above. Sleeve 808 may provide one or more anchoring protrusions 850 for engaging with clip 802 to prevent retrograde movement of clip 802 within cartridge 800. An intermediate sleeve 852 surrounding or enclosing innermost sleeve 808 may be provided with one or more advancement protrusions 854 that are configured to engage with and push clip 802 forward towards the distal end of mechanism 800. Advancement protrusions 854 are configured to protrude through a longitudinal groove or window 856 that is provided with innermost sleeve 808 to enable engaging with clip 802. In order to advance clip 802, anchoring protrusion 850 may engage with clip 802 and hold clip 802 in place while intermediate sleeve 852 is pulled back a predetermined distance, such as the length of a clip, towards the proximal end of cartridge 800. Intermediate sleeve 852 may then be advanced forward, causing advancement protrusion 854 to engage with clip 802, pulling it forward towards the distal end of cartridge 800. The most distally positioned advancement protrusion 854A of intermediate sleeve is configured to engage and position the most distal clip 802 to a deployable position within a pair of integral jaws 856 of innermost sleeve, such as by being held in place by one or more grooves provided with jaws 234.

Protrusion 854A may be biased by outermost sleeve 810, disposed with sharp tip 804 and corresponding to outer sleeve 110 of FIG. 1A, in a manner to engage clip 802 only when clip 802 is being advanced. Upon positioning clip 802 for deployment at the distal end of cartridge 800, protrusion 854A extends past the distal end of outermost sleeve 810, thereby no longer engaging with clip 802. Any further advancement by intermediate sleeve 852 serves to compress clip 802.

Intermediate sleeve 852 may be advanced over innermost sleeve 808 (not shown) and clip arms 812a and 812b, thereby compressing arms 812a and 812b and engaging locking mechanism 814 to lock over the tissue. Prongs, such as in any of the embodiments described above may be provided with either of clips 802 or sleeve 802 to activate the locking mechanism.

Advantageously, when there is one last clip for deployment within sleeve 808, advancement of outermost sleeve 810 over the integral jaws does not lock the clip, but rather only reversibly approximates clip arms 812a and 812b, thereby allowing the deployment of clip 802 when it is the last clip disposed within sleeve 808.

The following method describes multiple steps for deploying a clip using a micro-laparoscopic clip applier, in accordance with an embodiment of the invention. A clip applier is positioning to deploy a surgical clip housed in a rigid sleeve provided with the clip applier, where the sleeve houses multiple interconnected surgical clips, and each of the clips, when housed within the sleeve is closed and unlocked, and where each of the clips is provided with a self locking mechanism at its distal end and is normally-open by a proximal integral spring disposed with each of the clips. The clip arms of the interconnected clips housed in the sleeve may be oriented lengthwise along a length of the sleeve, and the clips may be made of superelastic material In some embodiments, exposing the clip may include perforating a body cavity wall with a Veress needle provided with the clip applier, where the Veress needle includes an inner sleeve with a blunt distal end, and an outer sleeve with a sharp distal end, and where the sleeve housing the clips comprises the inner sleeve, and where the distal end of the most distally-positioned clip comprises the blunt distal end, and where the clips are exposed via the perforation made by the sharp distal end.

A handle extending from the sleeve may be operated to advance the clips towards a distal end of the sleeve, and position a most distally positioned clip for deployment by exposing the clip from the distal end of the sleeve, where the exposing causes the clip to open.

Optionally, the clips may be advanced by a pusher, where portion of the pusher is alternately flexible for bending into a coil configuration allowing it to be stored in the handle, and alternately straight and rigid for advancing the clips in the sleeve. One or more ratchets may engage the pusher to control the advancement of the pusher from the coil configuration to the straight rigid pusher for advancing the clips.

A dial may be provided with the handle may be rotated to rotate the clips housed in the sleeve in synchrony with a rotation of the sleeve, where a ball and socket joint provided with the pusher enables the handle to remain stationary relative to the rotated clips.

The sleeve may be advanced relative to the exposed clip to close the exposed clip over a bodily tissue until the self locking mechanism of the exposed clip engages, thereby deploying the exposed clip, where an axial distance between the exposed clip and the handle throughout the sleeve advancing steps remains constant.

In some embodiments, advancing the sleeve relative to the exposed clip to close and lock the exposed clip further comprises applying a moment on the clip via one or more prongs provided with the clip applier. Optionally, the prongs may be disposed with the inner sleeve, and the self locking mechanism may be activated by engaging the prongs with one or more niches provided with the clips. Alternatively, the prongs may be disposed with the clip arms and the self locking mechanism may be activated by engaging the prongs with the sleeve.

In another embodiment, engaging the self locking mechanism comprises engaging a hook disposed at a distal end of one clip arm disposed with the exposed clip with the other clip arm of the exposed clip.

Upon closing and locking the clip, the sleeve may be retracted relative to the exposed clip to expose an interconnecting mechanism disposed at a proximal end of the exposed clip, to enable disconnecting the deployed clip from the remaining clips housed in the sleeve.

The following method describes multiple steps for deploying a clip using a micro-laparoscopic clip applier, in accordance with another embodiment of the invention. A clip applier is positioning to deploy a surgical clip housed in a rigid sleeve provided with the clip applier, where the sleeve houses multiple interconnected surgical clips, and each of the clips, when housed within the sleeve is closed and is normally-closed by a proximal integral spring disposed with each of the clips. The clip arms of the interconnected clips housed in the sleeve may be oriented lengthwise along a length of the sleeve, and the clips may be made of superelastic material In some embodiments, exposing the clip may include perforating a body cavity wall with a Veress needle provided with the clip applier, where the Veress needle includes an inner sleeve with a blunt distal end, and an outer sleeve with a sharp distal end, and where the sleeve housing the clips comprises the inner sleeve, and where the distal end of the most distally-positioned clip comprises the blunt distal end, and where the clips are exposed via the perforation made by the sharp distal end.

A handle extending from the sleeve may be operated to advance the clips towards a distal end of the sleeve, and position a most distally positioned clip for deployment by exposing the clip from the distal end of the sleeve.

Optionally, the clips may be advanced by a pusher, where portion of the pusher is alternately flexible for bending into a coil configuration allowing it to be stored in the handle, and alternately straight and rigid for advancing the clips in the sleeve. One or more ratchets may engage the pusher to control the advancement of the pusher from the coil configuration to the straight rigid pusher for advancing the clips.

A dial may be provided with the handle may be rotated to rotate the clips housed in the sleeve in synchrony with a rotation of the sleeve, where a ball and socket joint provided with the pusher enables the handle to remain stationary relative to the rotated clips.

The sleeve may be retracted relative to the exposed clip in a first step to open the exposed clip by compressing the hinge of the clip. The sleeve may be retracted relative to the exposed clip in a second step to close the exposed clip over a bodily tissue, where an axial distance between the exposed clip and the handle throughout the sleeve retracting steps may remain constant. The sleeve may be retracted further relative to the exposed clip to expose an interconnecting mechanism disposed at a proximal end of the exposed clip to enable disconnecting the exposed clip from the other clips housed in the sleeve.

Thus, by disposing a laparoscopic clip applier in accordance with the system and method described above, such as by employing a user friendly miniature advancement mechanism for maneuvering surgical clips within a retractable needle, specific minimally-invasive procedures medical procedures such as Cholecystectomy, removal of ovary, sterilization, hysterectomy, bariatric surgery, thoracoscopy, etc. can be easily performed by the present device, overcoming size constraint hurdles that are associated with prior art devices.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is to be understood that the following claims are to cover all generic and specific features of the invention described herein, and all statements of the scope of the invention which, as a matter of language, might be said to fall therebetween.

What is claimed is:

1. A laparoscopic clip applier comprising:
a proximal handle configured for controlling a position said clip applier;
a rigid sleeve extending from said handle;
a trigger connected to said sleeve to advance said sleeve distally with respect to said handle and to retract said sleeve proximally with respect to said handle in response to manipulating said trigger with respect to said handle in first direction and a second direction respectively;
multiple interconnected clips, each clip of said multiple interconnected clips being normally-open by a proximal spring integral to the clip,
wherein each said clip is housed in said sleeve, and
wherein each said clip is provided with a latch at its distal end, and
wherein each said clip, when housed within said sleeve, is closed and unlocked; and
a pusher operable to move with respect to said handle and engaged with the multiple interconnected clips to:
advance said multiple interconnected clips distally with respect to said handle and
to position a most distally-positioned clip of said multiple interconnected clips into a deployment position;
wherein retracting said sleeve with said trigger exposes said most distally-positioned clip from said distal end of said sleeve and causes said most distally-positioned clip to open while remaining in said deployment position axially stationary with respect to said handle,
wherein advancing said sleeve with said trigger, while said pusher retains said exposed most distally-positioned clip in said deployment position axially stationary with respect to the handle, closes said exposed most distally-positioned clip until said latch of said exposed most distally-positioned clip engages.

2. The clip applier of claim 1, further comprising a Veress needle comprising:
an outer sleeve with a sharp distal end for forming a perforation in an outer wall of a body cavity,
wherein said distal end of said most distally-positioned clip provides a blunt distal end for said rigid sleeve configured to pass through said perforation made by said sharp distal end of said outer sleeve.

3. The clip applier of claim 1, wherein each said clip of said multiple interconnected clips housed in said sleeve includes at least two arms oriented lengthwise along a length of said sleeve.

4. The clip applier of claim 1, wherein said multiple interconnected clips are made, at least partially, of super-elastic material.

5. The clip applier of claim 1, wherein said pusher is configured to maintain a constant axial distance between said exposed most distally-positioned clip and said handle throughout said advancing and retracting said rigid sleeve relative to said exposed most distally-positioned clip steps.

6. The clip applier of claim 1, wherein a diameter of said rigid sleeve is micro-laparoscopic.

7. The clip applier of claim 1, wherein a distal tip of said rigid sleeve is disposed with carved out slots configured to allow said rigid sleeve to advance over said exposed most distally positioned clip without pinching bodily tissue.

8. The clip applier of claim 1, wherein said trigger is configured to further retract said sleeve proximally relative to said handle, while said pusher retains said exposed most distally-positioned clip in said deployment position axially stationary with respect to the handle thereby exposing an interconnection between a proximal end of said exposed most distally-positioned clip and a distal end of a subsequent clip of said multiple interconnected clips; to allow disconnecting said most distally-positioned clip from said subsequent clip.

9. The clip applier of claim 1, wherein said trigger is distal to said handle.

10. The clip applier of claim 1, wherein said pusher is configured for axially positioning a subsequent clip of said multiple interconnected clips to said deployment position at a same axially position relative to said handle as for, said most distally-positioned clip.

11. The clip applier of claim, further comprising
a ratchet limiting movement of said pusher to advance a single clip at a time.

12. The clip applier of claim 1, further comprising one or more prongs, wherein said latch is configured to be activated by a moment applied on said exposed most distally-positioned clip by said prongs.

13. The clip applier of claim 12, wherein said prongs are disposed with any of: a) said rigid sleeve, and wherein said latch is configured to be activated by engaging said prongs with one or more niches provided with said exposed most distally-positioned clip, b) a pair of arms of said clip, and wherein said latch is configured to be activated by engaging said prongs with said advancing sleeve.

14. The clip applier of claim 1, wherein said latch comprises an elastic hook disposed at said distal end of said exposed most distally positioned clip, wherein said elastic hook is biased outwards, and wherein said elastic hook is folded inwards when said most distally positioned clip is housed within said sleeve and protrudes outwards when said most distally positioned clip is exposed from said sleeve.

15. The clip applier of claim 14, wherein a length of said elastic hook is greater than an inner diameter of said sleeve.

16. The clip applier of claim 1, wherein a proximal portion of said pusher is alternately flexible and configured to bend into a coil configuration thereby allowing said pusher to be housed in said handle, and a distal portion of said pusher is alternately straight and rigid and configured to advance said multiple interconnected clips in said sleeve.

17. The clip applier of claim 16, wherein said handle includes one or more protrusions configured to engage said pusher to control a movement of said pusher from said coil configuration to a straight rigid configuration when advancing said multiple interconnected clips.

18. The clip applier of claim 16, further comprising a dial configured to rotate said sleeve in synchrony with said multiple interconnected clips, wherein a ball and socket joint provided with said pusher is configured to enable said handle to remain axially stationary relative to said multiple interconnected clips while said sleeve rotates.

* * * * *